US012048714B2

(12) United States Patent
Rozhkova et al.

(10) Patent No.: US 12,048,714 B2
(45) Date of Patent: Jul. 30, 2024

(54) PRODUCTS AND METHODS FOR ORGAN PROTECTION WITH NOBLE NANOPARTICLES

(71) Applicant: UCHICAGO ARGONNE, LLC, Chicago, IL (US)

(72) Inventors: Elena A. Rozhkova, Lemont, IL (US); Elena Shevchenko, La Grange, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 197 days.

(21) Appl. No.: 16/843,114

(22) Filed: Apr. 8, 2020

(65) Prior Publication Data

US 2021/0315929 A1   Oct. 14, 2021

(51) Int. Cl.
| | | |
|---|---|---|
| *A61K 33/242* | (2019.01) | |
| *A01N 1/02* | (2006.01) | |
| *A61K 9/51* | (2006.01) | |
| *A61P 39/06* | (2006.01) | |
| *G01N 33/50* | (2006.01) | |

(52) U.S. Cl.
CPC .......... *A61K 33/242* (2019.01); *A61K 9/5115* (2013.01); *A61P 39/06* (2018.01); *G01N 33/502* (2013.01)

(58) Field of Classification Search
None
See application file for complete search history.

(56) References Cited

U.S. PATENT DOCUMENTS 4,829,984 A * 5/1989 Gordon ................ A01N 1/0294
424/617
2009/0305224 A1 * 12/2009 He ....................... A01N 1/0278
435/2

OTHER PUBLICATIONS

Wang, Jianling, et al. "In vivo self-bio-imaging of tumors through in situ biosynthesized fluorescent gold nanoclusters." Scientific reports 3.1 (2013): 1-6. (Year: 2013).*
Wang, Yanyan, et al. "Potent selective inhibition of MMP-14 by chloroauric acid and its inhibitory effect on cancer cell invasion." RSC Advances 5.23 (2015): 17700-17708. (Year: 2015).*
Neshatian, Mehrnoosh, et al. "Uptake of gold nanoparticles in breathless (hypoxic) cancer cells." Journal of biomedical nanotechnology 11.7 (2015): 1162-1172. (Year: 2015).*
Lai, Lanmei, et al. "Fluorescent gold nanoclusters for in vivo target imaging of Alzheimer's disease." RSC advances 6.36 (2016): 30081-30088. (Year: 2016).*
Correia, Sónia C., and Paula I. Moreira. "Hypoxia-inducible factor 1: a new hope to counteract neurodegeneration?. " Journal of neurochemistry 112.1 (2010): 1-12. (Year: 2010).*
Mansfield, Kyle D., M. Celeste Simon, and Brian Keith. "Hypoxic reduction in cellular glutathione levels requires mitochondrial reactive oxygen species." Journal of Applied Physiology 97.4 (2004): 1358-1366. (Year: 2004).*
Yoo, Heon, et al. "Expression of the hypoxia marker carbonic anhydrase 9 is associated with anaplastic phenotypes in meningiomas." Clinical cancer research 13.1 (2007): 68-75. (Year: 2007).*
McFaline-Figueroa, J. Ricardo, and Eudocia Q. Lee. "Brain tumors." The American journal of medicine 131.8 (2018): 874-882. (Year: 2018).*
Wang et al., A redox interaction-engaged strategy for multicomponent nanomaterials, Chem. Soc. Rev., 49:736-764 (2020).
Wang et al., Hierarchical Nanocomposites of Polyaniline Nanowire Arrays on Reduced Graphene Oxide Sheets for Supercapacitors, Scientific Reports, 3:3568:1-9 (2013).
Xue et al., Generation of three-dimensional retinal tissue with functional photoreceptors from human iPSCs, Nat. Commun., 5:4047 (2014).
Yagi, A scanning SAXS/WAXS study of rat brain, J. Phys. Conf. Ser., 272:012009 (2011).
Ye et al., Rapid and accurate tumor-target bio-imaging through specific in vivo biosynthesis of a fluorescent europium complex, Biomater Sci., 4:652-60 (2016).
Ying, Nad+ and NADH in brain functions, brain diseases and brain aging, Front. Biosci., 12:1863-1888 (2007).
Zhang et al., NAD? repletion improves mitochondrial and stem cell function and enhances life span in mice, Science, 352:1436-1443 (2016).
Zhu et al., In vivo NAD assay reveals the intracellular NAD contents and redox state in healthy human brain and their age dependences, PNAS., 112(9):2876-2881 (2015).
Agmon et al., Thalamocortical responses of mouse somatosensory (barrel) cortex in vitro, Neuroscience, 41:365-79 (1991).
Alberti, The biochemical consequences of hypoxia, J. Clin. Pathol. Suppl. (R. Coll. Pathol.), 11:14-20 (1977).
Aon et al., Protective mechanisms of mitochondria and heart function in diabetes, Antioxid Redox Signal, 22:1563-86 (2015).
Atukeren, The Impact of Redox Balance in Brain Tumors, in Molecular Targets of CNS Tumors edited by Miklos Garami, 15 pages (2011).
Benjamin et al., Heart Disease and Stroke Statistics—2017 Update: A Report From the American Heart Association, Circulation, 135:e146-e603 (2017).
Berthiaume et al., Mitochondrial NAD+/NADH Redox State and Diabetic Cardiomyopathy, Antioxidants & Redox Signaling, 30(3): 375-398 (2019).
Blakemore, Magnetotactic bacteria, Science, 190:377-379 (1975).
Busl et al., Hypoxic-ischemic brain injury: pathophysiology, neuropathology and mechanisms, NeuroRehabilitation, 26:5-13 (2010).

(Continued)

*Primary Examiner* — Bong-Sook Baek
*Assistant Examiner* — Peter Anthopolos
(74) *Attorney, Agent, or Firm* — MARSHALL, GERSTEIN & BORUN LLP

(57) ABSTRACT

Products and methods for redirecting the pathological biochemical process of accumulation of reduced pyridine nucleotides under deleterious hypoxia conditions toward the reduction of the precursor salt and the biosynthesis of biologically compatible, antioxidant noble metal nanoparticles and the simultaneous restoring of the tissue redox state are provided. The products and methods have application in the treatment of hypoxia and hypoxia-related diseases and disorders. Such products and methods are also useful in organ transplantation and recovery, in screening of anti-hypoxia agents, and in detecting elevated levels of the reducing equivalents of the redox state, for example, NADH, NADPH, GSH, and $TrxSH_2$, in cells, tissues, or organs.

12 Claims, 5 Drawing Sheets

(56) References Cited

OTHER PUBLICATIONS

Caccavo et al., Geobacter sulfurreducens sp. nov., a hydrogen- and acetate-oxidizing dissimilatory metal-reducing microorganism, Appl. Environ. Microb., 60:3752-3759 (1994).
Chen et al., In Situ Biosynthesis of Fluorescent Platinum Nanoclusters: Toward Self-Bioimaging-Guided Cancer Theranostics, Acs. Appl. Mater Inter., 7:18163-18169 (2015).
Coupland et al., The definition of stroke, J. R. Soc. Med., 110:9-12 (2017).
Dreaden et al., The golden age: gold nanoparticles for biomedicine, Chemical Society Reviews, 41:2740-79 (2012).
Estevez et al., Neuroprotective mechanisms of cerium oxide nanoparticles in a mouse hippocampal brain slice model of ischemia, Free Radical Bio. Med., 51:1155-1163 (2011).
Esumi et al., Antioxidant-potentiality of gold-chitosan nanocomposites, Colloids and Surfaces B: Biointerfaces, 32:117-123 (2003).
Farooq et al., Gold nanoparticles-enabled efficient dual delivery of anticancer therapeutics to HeLa cells, Sci. Rep., 8:2907 (2018).
Fernandez et al., Intracellular accumulation and immunological properties of fluorescent gold nanoclusters in human dendritic cells, Biomaterials, 43:1-12 (2015).
Gao et al., Ligand modified nanoparticles increases cell uptake, alters endocytosis and elevates glioma distribution and internalization, Sci. Rep., 4:5138 (2014).
Garofalo et al., Brain levels of NADH and NAD+ under hypoxic and hypoglycaemic conditions in vitro, J. Neurochem., 51:172-176 (1988).
Giljohann et al., Gold nanoparticles for biology and medicine, Angew Chem. Int. Ed., 49:3280-3294 (2010).
Gomes et al., Declining NAD(+) induces a pseudohypoxic state disrupting nuclear-mitochondrial communication during aging, Cell, 155:1624-1638 (2013).
He et al., Intrinsic catalytic activity of Au nanoparticles with respect to hydrogen peroxide decomposition and superoxide scavenging, Biomaterials, 34:765-773 (2013).
Heckman et al., Custom cerium oxide nanoparticles protect against a free radical mediated autoimmune degenerative disease in the brain, ACS Nano., 7:10582-10596 (2013).
Heidelberg et al., Genome sequence of the dissimilatory metal ion-reducing bacterium Shewanella oneidensis, Nat. Biotechnol., 20:1118-23 (2002).
Huang et al., Gold nanoparticles: catalyst for the oxidation of NADH to NAD(+), J Photochem. Photobiol. B., 81:76-83 (2005).
Jin et al., Rapid in situ biosynthesis of gold nanoparticles in living platelets for multimodal biomedical imaging, Colloids Surf. B. Biointerfaces, 163:385-93 (2018).
Kim et al., Ceria nanoparticles that can protect against ischemic stroke, Angew Chem. Int. Ed., 51:11039-11043 (2012).
Kim et al., Stimuli-responsive magnetic nanomicelles as multifunctional heat and cargo delivery vehicles, Langmuir, 29:7425-7432 (2013).
Kim et al., Synthesis of Hybrid Gold/Iron Oxide Nanoparticles in Block Copolymer Micelles for Imaging, Drug Delivery, and Magnetic Hyperthermia, IEEE T. Magn., 45:4821-4824 (2009).
Kwon et al., Heterogeneous nucleation and shape transformation of multicomponent metallic nanostructures, Nat. Mater, 14:215-223 (2015).
Kwon et al., Mitochondria-Targeting Ceria Nanoparticles as Antioxidants for Alzheimer's Disease, ACS Nano., 10:2860-2870 (2016).
Lee et al., Targeted multimodal nano-reporters for pre-procedural MRI and intra-operative image-guidance, Biomaterials, 109:69-77 (2016).
Li et al., Mechanism of pH-switchable peroxidase and catalase-like activities of gold, silver, platinum and palladium, Biomaterials, 48:37-44 (2015).
Li et al., Small angle X-ray scattering for nanoparticle research, Chem. Rev., 116:11128-11180 (2016).
Magistretti et al., Cellular mechanisms of brain energy metabolism. Relevance to functional brain imaging and to neurodegenerative disorders, Ann. N. Y. Acad. Sci., 777:380-387 (1996).
McNamara et al., Nanoparticles in biomedical applications, Adv. Phys: X, 2:54-88 (2017).
Methe et al., Genome of Geobacter sulfurreducens: metal reduction in subsurface environments, Science, 302:1967-1969 (2003).
Murphy et al., Gold nanoparticles in biology: beyond toxicity to cellular imaging, Acc. Chem. Res., 41:1721-1730 (2008).
Pedone et al., Platinum nanoparticles in nanobiomedicine, Chem. Soc. Rev., 46:4951-4975 (2017).
Pilapong et al., Visualizing reactive oxygen species inside cancer cells after stimulation with polycyclic aromatic hydrocarbon via spontaneous formation of Au nanoclusters, Mater. Lett., 140:162-165 (2015).
Rozhkova et al., Hypoxia-Induced Biosynthesis of Gold Nanoparticles in the Living Brain, Nanoscale, 11: 19285-19290 (2019).
Rozhkova et al., Interactions between the isolated oxygenase and reductase domains of neuronal nitric-oxide synthase: assessing the role of calmodulin, J. Biol. Chem., 277:16888-16894 (2002).
Rozhkova, Nanoscale materials for tackling brain cancer: recent progress and outlook, Adv. Mater., 23:H136-H150 (2011).
Sadovsky et al., Scaling of topologically similar functional modules defines mouse primary auditory and somatosensory microcircuitry, J. Neurosci., 33:14048-60 (2013).
Seckback, Ferreting out the secrets of plant ferritin—A review, J. Plant Nutr., 5:369-394 (1982).
Shibuya et al., Palladium and platinum nanoparticles attenuate aging-like skin atrophy via antioxidant activity in mice, PLoS ONE, 9(10):e109288 (2014).
Thakor et al., Gold nanoparticles: a revival in precious metal administration to patients, Nano. Lett., 11:4029-36 (2011).
Valgimigli et al., Antioxidant activity of nanomaterials, J. Mater. Chem. B., 6:2036-2051 (2018).
Vitol et al., Efficient Cisplatin Pro-Drug Delivery Visualized with Sub-100 nm Resolution: Interfacing Engineered Thermosensitive Magnetomicelles with a Living System, Adv. Mater. Interfaces, 1:1400182 (2014).
Vitol et al., Microfabricated magnetic structures for future medicine: from sensors to cell actuators, Nanomedicine, 7:1611-1624 (2012).
Vrselja et al., Restoration of brain circulation and cellular functions hours post-mortem, Nature, 568:336-343 (2019).

\* cited by examiner

FIG. 4A Coronal section plane

Right hemisphere (Treated) | Left hemisphere (Control)

FIG. 5A
FIG. 5B
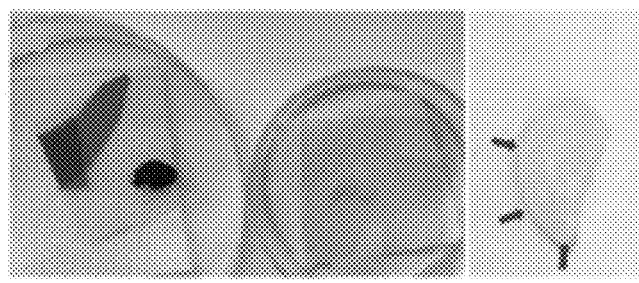
FIG. 6
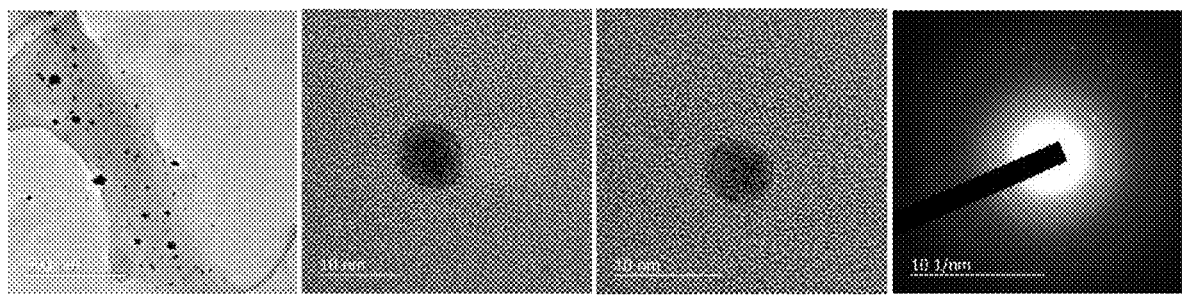

PRODUCTS AND METHODS FOR ORGAN PROTECTION WITH NOBLE NANOPARTICLES

STATEMENT REGARDING FEDERALLY SPONSORED RESEARCH OR DEVELOPMENT

This invention was made with government support under Contract No. DE-AC02-06CH11357 awarded by the United States Department of Energy, Office of Science, under Contract No. DE-AC02-06CH11357. The government has certain rights in the invention.

FIELD

Products and methods for redirecting the pathological biochemical process of accumulation of reduced pyridine nucleotides under deleterious hypoxia conditions toward the reduction of the precursor salt and the biosynthesis of biologically compatible, antioxidant gold nanoparticles and the simultaneous restoring of the tissue redox state are provided. The products and methods have application in the treatment of hypoxia, in organ transplantation and recovery, in screening of anti-hypoxia therapeutics, and in detecting elevated levels of the reducing equivalents NAD(P)H in cells and tissues.

BACKGROUND

Hypoxia, or lack of oxygen, leads to disruption and cessation of all vital energetic and metabolic pathways, which is equivalent to a death sentence for cells, tissues and organs. The brain is a particularly sensitive organ to oxygen depletion with irreversible changes occurring within a minute (Alberti, J Clin Pathol Suppl (R Coll Pathol), 1977, 11:14-20). Representing only 2% of the body weight, the brain consumes about 15% of all blood pumped by the heart, and 20% of the total oxygen supply to the body (Magistretti et al., Ann N Y Acad Sci, 1996, 777: 380-387). One of the most life-threatening diseases mediated by hypoxia is stroke (Coupland et al., J R Soc Med, 2017, 110: 9-12). First described by the father of medicine, Hippocrates, more than 2,400 years ago, stroke or "brain attack" remains one of the main causes of global mortality. For example, in the US stroke kills someone every four minutes (Benjamin et al., Circulation, 2017, 135: e146-e603). Although underlying causes for oxygen deprivation in the brain can be various, and the mechanisms of the brain injury by hypoxia are quite complex and not completely understood, the distinctive hallmarks of this pathology are well-established. These hallmarks include suppression of electron transfer pathways, impaired adenosine triphosphate (ATP) levels (Busl et al., NeuroRehabilitation, 2010, 26: 5-13), deficiency of oxidized forms of nicotinamide adenine dinucleotide (NAD) cofactor, and, accordingly, an increase in the NADH/NAD+ ratio (Garofalo et al., J Neurochem, 1988, 51:172-176), which leads to excessive production of reactive oxygen species (ROS), reactive nitrogen species (RNS) and induction of programmed cell death, or apoptosis (Busi et al., supra). NAD+, discovered in 1906, regained attention as a result of recognizing its role in supporting essential bioenergy processes (Ying, Front Biosci-Landmrk, 2007, 12: 1863-1888; Zhang et al., Science, 2016, 352: 1436-1443; Gomes et al., Cell, 2013, 155: 1624-1638).

Under healthy conditions, NAD co-enzymes play an important role in the brain energetics and function, including neurotransmission, learning and memory (Magistretti et al., Ann N Y Acad Sci, 1996, 777; 380-387; Ying, supra). Severe hypoxia in the brain can lead to more than 200% increase in the concentration of NADH (Garofolo et al., supra). Such a morbid accumulation of the reduced form of this cofactor during hypoxia activates enzymes such as NADH-dependent oxidases and nitric oxide synthases (e.g. iNOS) and, consequently, neuronal tissue breakdown and the brain injury by ROS and RNS. Existing anti-hypoxia medicinal treatments can be aimed at interfering one or another specific pathologic pathways, however a more universal approach to combating hypoxia remains challenging.

Nanoparticles (NPs) are extensively studied for their applications in biomedicine for therapy and diagnostics (Rozhkova, Adv Mater, 2011, 23: H136-H150; Vitol et al., Nanomedicine-UK, 2012, 7: 1611-1624; Lee et al., Biomaterials, 2016, 109: 69-77; Kim et al., Langmuir, 2013, 29: 7425-7432; Vitol et al., Adv Mater Interfaces, 2014, 1; Kim, et al., Ieee T Magn, 2009, 45: 4821-4824; Farooq et al., Sci Rep-Uk, 2018, 8; McNamara et al., Adv Phys-X, 2017, 2: 54-88). Moreover, nanoparticles can be used for neuroprotection (Kim et al., Angew Chem Int Ed 2012, 51: 11039-11043; Estevez et al., Free Radical Bio Med, 2011, 51: 1155-1163; Heckman et al., ACS Nano, 2013, 7: 10582-10596; Kwon et al., ACS Nano, 2016, 10: 2860-2870). However, most studies focus on the use of pre-synthetized NPs. The functionality of NPs is related to their physical properties, for example, their ability to interact with external stimuli, such as photons, magnetic field, temperature, pH, sound, and their ability to deliver the desired molecules, such as polypeptides, DNA, and contrasting and therapeutic agents, to target sites (McNamara, Adv Phys-X, 2017, 2: 54-88).

Gold (Au)-based nanostructures are very appealing for biomedical applications owing to their high biocompatibility and in vivo stability (Farooq, et al. Sci Rep-Uk, 2018, 8; Giljohann, et al., Angew Chem Int Ed, 2010, 49: 3280-3294; Murphy et al., Accounts Chem Res, 2008, 41: 1721-1730; Thakor et al., Nano Lett, 2011, 11, 4029-4036). Moreover, the inherent antioxidant properties of Au NPs (Valgimigli et al., J Mater Chem B, 2018, 6: 2036-2051) as various ROS scavengers (Esumi et al., Colloid Surface B, 2003, 32: 117-123; He et al., Biomaterials, 2013, 34: 765-773; Li et al., Biomaterials, 2015, 48: 37-44) add remarkable value to their tissues protection potential.

There remains a need in the art for means for changing the redox state of a cell undergoing hypoxia or at risk of undergoing hypoxia. The ability to manipulate the redox state of the cell will have useful applications in the treatment of hypoxia, in the treatment of hypoxia-related diseases and disorders, in organ transplantation and recovery, and in screening of anti-hypoxia agents.

SUMMARY

Provided herein are products and methods for changing an oxidation-reduction (redox) state of a cell undergoing or at risk of undergoing hypoxia. In some aspects, a method of the disclosure comprises administering to the cell an effective amount of a noble metal precursor so that the noble metal precursor forms a noble metal nanoparticle (NP) in-situ in the immediate vicinity of the hypoxia site, thereby restoring the redox state of the cell, tissue or organ suffering or at risk of suffering hypoxia or oxidative stress. Such products and methods have useful applications in the treatment of hypoxia-related diseases and disorders, in organ transplantation and recovery, in screening of anti-hypoxia agents, and in detecting elevated levels of the reducing equivalents of the redox state, for example, NADH, NADPH, GSH, and TrxSH2, of cells, tissues, and/or organs. In various aspects, cells, tissues, and/or organs includes biopsied material and/or isolated cell, tissues, and/or organs.

In some aspects, the disclosure provides a method of changing the redox state of a cell undergoing or at risk of undergoing hypoxia, the method comprising administering to the cell an effective amount of a noble metal precursor. In some aspects, changing the redox state of the cell comprises increasing the ratio of oxidized to reduced forms of nicotinamide adenine dinucleotide (NAD+/NADH), nicotinamide adenine dinucleotide phosphate (NADP+/NADPH), glutathione (GSSG/GSH), or thioredoxin (TrxSS/TrxSH$_2$) in the cell. In some aspects, increasing the ratio of NAD+/NADH, NADP+/NADPH, GSSG/GSH, or TrxSS/TrxSH$_2$ reduces the production of reactive oxygen species, reduces production of reactive nitrogen species, and/or reduces apoptosis. In some aspects, changing the redox state of the cell comprises conversion of the noble metal precursor to a biocompatible antioxidant noble metal nanoparticle in the cell or in the vicinity of the cell. In some aspects, the noble metal nanoparticle reduces the accumulation of reduced pyridine nucleotides in the cell or in the vicinity of the cell. In some aspects, the cell is suffering from or is at risk of suffering from a deficiency of oxidized forms of nicotinamide adenine dinucleotide (NAD+), nicotinamide adenine dinucleotide phosphate (NADP+), glutathione (GSSG), or thioredoxin (TrxSS). In some aspects, NADH is converted to NAD+, NADPH is converted to NADP+, GSH is converted to GSSG, or TrxSH$_2$ is converted to TrxSS.

In some aspects of the disclosure, the noble metal precursor is gold (Au), silver (Ag), platinum (Pt), palladium (Pd), ruthenium (Ru), rhodium (Rh), osmium (Os), or iridium (Ir), or the noble metal precursor a noble metal halide, hydroxide, or a complex thereof with one or more organic ligands, or combinations thereof. In some aspects, the noble metal precursor is a gold chloride. In some aspects, the gold chloride is gold monochloride (AuCl), gold dichloride (AuCl$_2$), gold trichloride (AuCl$_3$), tetragold octachloride (Au$_4$Cl$_8$), or chloroauric acid (HAuCl$_4$).

In some aspects, the cell is in a tissue or organ suffering from or at risk of suffering from a hypoxic condition, such as oxidative stress, oxygen free radical damage, and/or ischemia-reperfusion injury. In some aspects, the cell is a neuronal cell, a cardiac cell, a kidney cell, a lung cell, a liver cell, a stomach cell, an intestinal cell, a pancreatic cell, a blood cell, a retinal cell, a skin cell, or other cell of the eye. In some aspects, the cell is tumor cell. In some aspects, the tumor cell is a cancer cell. In some aspects, the cell undergoing or at risk of undergoing hypoxia is in a tissue or organ that is being preserved for transplantation, for testing components of the redox state, or for screening an anti-hypoxia agent. In some aspects, the cell undergoing or at risk of undergoing hypoxia is in a tissue or organ in a subject suffering from a hypoxia-related disorder.

In some aspects, such hypoxia-related disorder is chronic inflammation, an inflammatory disorder, a neurodegenerative disease, a retinal disease, hyperglycemia, diabetes, thrombosis, a cardiovascular disease, chronic fatigue syndrome, asthma, chronic obstructive pulmonary disease, infertility, ulcer, bacterial infection, sepsis, gangrene, or cancer. In some aspects, the cell is in a subject. In some aspects, the subject is a mammal. In some aspects, the mammal is a human. In some aspects, the administering is carried out intravenously, intranasally, intracerebrally, intracisternally, and/or intracerebroventricularly.

The disclosure therefore includes methods of ameliorating, treating, or preventing hypoxia or a hypoxic condition in a subject, the method comprising administering an effective amount of a noble metal precursor to the subject. In the subject, the noble metal precursor forms noble metal nanoparticles and thereby changes the redox state of cells, tissues, or organs in the subject suffering from the hypoxic condition.

The disclosure also includes one or more methods for screening an agent for its antioxidant activity, the method comprising exposing a cell, a plurality of cells, or a tissue to a noble metal precursor in the presence or absence of an agent indicated to have antioxidant activity; exposing the cell, the plurality of cells, or the tissue to a hypoxic condition or an oxidative stress; and measuring the conversion of the noble metal precursor to noble metal nanoparticles in or near the vicinity of the cell, the plurality of cells, or the tissue, wherein the agent is considered to have antioxidant activity if there is (i) a decrease in the concentration of noble metal precursor in the presence but not in the absence of the agent, (ii) an increase in the formation of noble metal nanoparticles in the presence but not in the absence of the agent, (iii) a decrease in the level of NADH, NADPH, GSH, or TrxSH2 in the presence but not in the absence of the agent, and/or (iv) an increase in the level of NAD+, NADP+, GSSG, or TrxSS in the presence but not in the absence of the agent. In various aspects, therefore, the agent is a candidate drug or therapeutic agent which either affects the redox state of the cell or affects the rate of formation of noble metal nanoparticles from the noble metal precursor. In various aspects, cells or the tissue includes biopsied material and/or otherwise isolated cells or tissues.

Other features and advantages of the disclosure will become apparent from the following description of the drawing and the detailed description. It should be understood, however, that the drawing, detailed description, and the examples, while indicating embodiments of the disclosed subject matter, are given by way of illustration only, because various changes and modifications within the spirit and scope of the disclosure will become apparent from the drawing, detailed description, and the examples.

BRIEF DESCRIPTION OF THE DRAWINGS

FIGS. 2E-G demonstrate the integrated SAXS intensities in the selected q ranges.

FIGS. 4A-D provides a schematic depiction of a coronal (frontal) plane mouse brain sectioning (FIG. 4A). The animal's brain was quickly dissected and sectioned on vibratome at a thickness of 450 µm (resulting tissue cross-section, FIG. 4B) (see Agmon et al., Neuroscience, 1991, 41:365-79), and then placed into an oxygenated incubation solution for 40 min, maintained at 32-36° C. (see Sadovsky et al., J. Neuroscience 2013, 33: 14048-60). Tissue sections were left to rest at room temperature for 30 min before hypoxic induction. Hypoxia was induced by placing the slices into a gas-tight chamber and terminating the oxygen flow for 5 min. Then $AuCl_3$ NPs precursor was added to the right hemisphere brain slice, while the left contralateral hemisphere was used as untreated control.

FIGS. 5A-B provide hypoxic brain sections after incubation with 10 mM (FIG. 5A, left) and 100 µM AuCl3 (FIG. 5B). The slices were exposed to higher 10 mM $AuCl_3$ under hypoxic (on the left) and oxygenated (on the right) conditions (FIG. 5A). While a hypoxic brain slice (on the left) after treatment with 10 mM $AuCl_3$ shows significant dark staining, the oxygenated brain slice (on the right) preserves its natural color (since pale yellowish color is a result of its fixation with paraformaldehyde/glutaraldehyde fixative solution). The hypoxic slice treated with 100 µM $AuCl_3$ before the fixation (FIG. 5B) clearly shows the pink staining mainly in the outer regions of the brain section (red arrows) due to the formation of NPs.

FIG. 6 provides transmission electron microscopy (TEM) images showing Au NPs formed in the hypoxic brain overloaded with 10 mM $AuCl_3$ precursor.

DETAILED DESCRIPTION

Figure 1A:
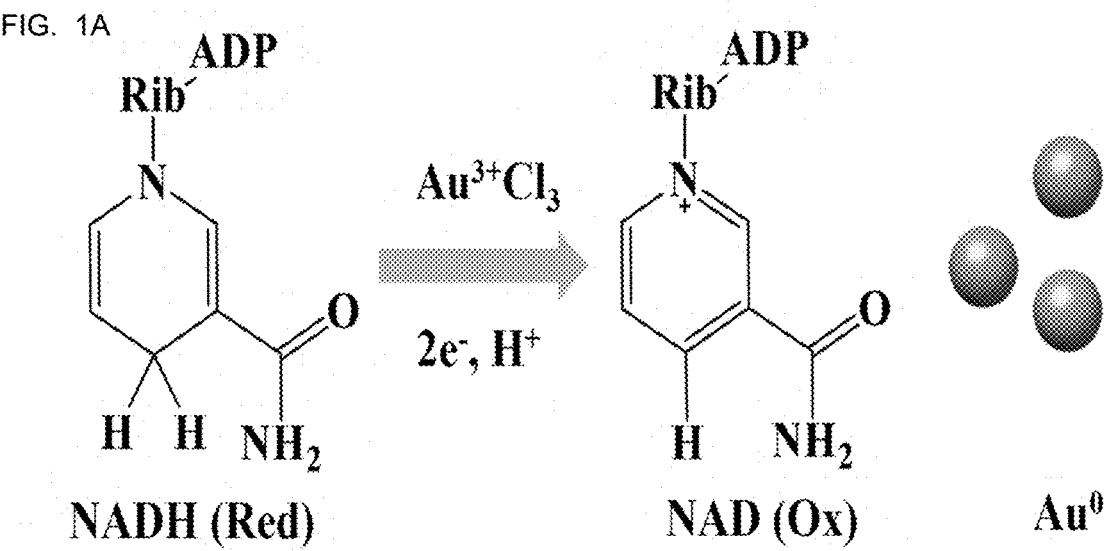
FIGS. 1A-B shows a reaction scheme depicting the transformation of AuCl$_3$ into Au0 NPs by NADH (FIG. 1A) and dynamics of the UV-vis spectra of NADH upon addition of AuCl$_3$, namely, decrease of signal intensity at ~320 nm corresponding to NADH and development of a new signal at ~520 nm corresponding to Au NPs (FIG. 1B). The molar ratios of AuCl$_3$ to NADH were 1:4, 1:2 and 3:2 upon first, second and third introductions of AuCl$_3$ solution into 100 µM NADH solution. The inset shows the cuvette with synthetized Au NPs.

The products and methods described herein are used in the targeted biosynthesis of biocompatible noble metal nanoparticles (NPs) from a noble metal precursor salt in-situ in the immediate vicinity of the hypoxia site, thereby restoring the redox state of the tissue or organ suffering oxidative stress or hypoxia. Products and methods are described herein for redirection of the pathological biochemical process of accumulation of reduced pyridine nucleotides under deleterious hypoxic conditions in the organ or tissue vulnerable to oxygen deficiencies and/or suffering hypoxia (e.g., brain, heart, kidney, lungs, liver and the like) toward the reduction of the precursor salt and biosynthesis of biologically compatible, antioxidant noble metal (e.g., $Au^0$) NPs and the simultaneous restoring of the tissue redox state. The proposed concept of biosynthesis of noble metal NPs triggered by a misbalance of the cellular pathological process (e.g., here by hypoxia), can complement the more classical use of pre-synthetized noble metal NPs.

Such approach can be implemented in other highly metabolic tissues and organs that are particularly vulnerable to oxygen deficiencies. Combined with innovative technologies for preserving and restoring the functions of isolated tissue at ambient conditions, for example BEx technology, the products and methods described herein can be utilized in the treatment and/or prevention of hypoxia, in organ transplantation and recovery, for combinatorial screening of an anti-hypoxia agent, e.g., an anti-hypoxia drug or therapeutic, on isolated sections of the living brain or other organ, and in the detection of abnormally elevated levels of the reducing equivalents NAD(P)H in cells, tissues and/or organs. In various aspects, cells, tissues, and/or organs includes biopsied material and/or isolated cell, tissues, and/or organs.

Provided herein are products and methods for changing an oxidation-reduction (redox) state of a cell undergoing or at risk of undergoing hypoxia. In some aspects, a method of the disclosure comprises administering to the cell an effective amount of a noble metal precursor so that the noble metal precursor forms a noble metal nanoparticle (NP) in-situ in the immediate vicinity of the hypoxia site, thereby restoring the redox state of the cell, tissue or organ suffering or at risk of suffering hypoxia or oxidative stress. Such products and methods have useful applications in the treatment of hypoxia-related diseases and disorders, in organ transplantation and recovery, in screening of anti-hypoxia agents, and in detecting elevated levels of the reducing equivalents of the redox state, for example, NADH, NADPH, GSH, and TrxSH2, of cells, tissues, and/or organs. In various aspects, cells, tissues, and/or organs includes biopsied material and/ or isolated cell, tissues, and/or organs.

Some embodiments provided herein provides a method of changing the redox state of a cell undergoing or at risk of undergoing hypoxia, the method comprising administering to the cell an effective amount of a noble metal precursor. In some aspects, changing the redox state of the cell comprises increasing the ratio of oxidized to reduced forms of nicotinamide adenine dinucleotide (NAD+/NADH), nicotinamide adenine dinucleotide phosphate (NADP+/NADPH), glutathione (GSSG/GSH), or thioredoxin (TrxSS/TrxSH2) in the cell. In some aspects, increasing the ratio of NAD+/NADH, NADP+/NADPH, GSSG/GSH, or TrxSS/TrxSH2 reduces the production of reactive oxygen species, reduces production of reactive nitrogen species, and/or reduces apoptosis. In some aspects, changing the redox state of the cell comprises conversion of the noble metal precursor to a biocompatible antioxidant noble metal nanoparticle in the cell or in the vicinity of the cell. In some aspects, the noble metal nanoparticle reduces the accumulation of reduced pyridine nucleotides in the cell or in the vicinity of the cell. In some aspects, the cell is suffering from or is at risk of suffering from a deficiency of oxidized forms of nicotinamide adenine dinucleotide (NAD+), nicotinamide adenine dinucleotide phosphate (NADP+), glutathione (GSSG), or thioredoxin (TrxSS). In some aspects, NADH is converted to NAD+, NADPH is converted to NADP+, GSH is converted to GSSG, or TrxSH2 is converted to TrxSS.

The term "redox," "redox status," or "redox state" is used herein to describe the balance between oxidants (or prooxidants) and antioxidants or the balance between the levels of oxidized and reduced species of redox couples, e.g., the four main redox couples, i.e., NADH/NAD+, NADPH/ NADP+, GSH/GSSG, and $TrxSH_2$/TrxSS in a biological system, such as a cell or organ. Cellular processes depend on the intracellular redox state. Aging cells undergo changes in redox homeostasis and acquire high levels of reactive oxygen species (ROS). Because accumulation of ROS involves a change in the redox state of cells, functions that are involved in setting redox and maintaining redox homeostasis are important in maintaining cell, tissue, and organ function. In some aspects, the term "redox" refers to the four main redox couples in a cell, which are NADH/NAD+, NADPH/NADP+, GSH/GSSG, and $TrxSH_2/TrxSS$. These couples are, to a certain extent, inter-convertible. The redox environment is a metric defined by the contribution of the different redox couples as a function of both their redox potential and the concentration of the reduced species.

The disclosure provides products and methods for the targeted biosynthesis of biocompatible noble metal nanoparticles (NPs) from a noble metal precursor salt in-situ in the immediate vicinity of the hypoxia site, thereby restoring the redox state of the cell, tissue or organ suffering oxidative stress or hypoxia. These methods can be carried out in vivo, ex vivo, or in vitro. Oxidative stress is an imbalance between free radicals and antioxidants in the body of an animal, including that of a human, which can lead to cell and tissue damage. The body's cells produce free radicals during normal metabolic processes. However, cells also produce antioxidants that neutralize these free radicals. In general, the body is able to maintain a balance between antioxidants and free radicals, but there are factors which can contribute to oxidative stress and excess free radical production, such as diet, lifestyle, certain health conditions, inflammation, the body's immune response, and environmental factors, such as pollution and radiation. In some aspects, the disclosure provides products and methods to decrease or neutralize such excess free radicals.

Cells contain mitochondria, which work to generate energy in the form of adenosine triphosphate (ATP). Mitochondria combine oxygen and glucose to produce carbon dioxide, water, and ATP. Free radicals arise as byproducts of this metabolic process. Free radicals, e.g., superoxide, hydroxyl radical, and nitric oxide radical, are oxygen-containing molecules with an uneven number of electrons. The uneven number allows them to easily react with other molecules causing the free radical to stabilize and become less reactive. Unsatisfied free radicals can spur the mutation of cells they encounter and, thus, play a role in aging and in causing and/or contributing to the progression of a variety of diseases including, but not limited to, chronic inflammation, inflammatory disorders, neurodegenerative diseases (such as, for example, Alzheimer's disease, amyotrophic lateral sclerosis (ALS), and Parkinson's disease), retinal disease, diabetes, cardiovascular diseases (such as, for example, high blood pressure, atherosclerosis, myocardial infarction, and stroke), chronic fatigue syndrome, ulcer, asthma, chronic obstructive pulmonary disease, and infertility. The products and methods of the disclosure for the targeted biosynthesis of biocompatible noble metal nanoparticles (NPs) from a noble metal precursor salt reduce the number of free radicals.

The mitochondrion is a major source of reactive oxygen species (ROS), such as peroxide ($O_2^{2-}$, $R_1OOR_2$), superoxide ($O_2(*-)$), or singlet oxygen. Superoxide ($O_2(*-)$), for example, is generated under specific bioenergetic conditions at several sites within the electron-transport system; most is converted to $H_2O_2$ inside and outside the mitochondrial matrix by superoxide dismutases. $H_2O_2$ is a major chemical messenger that, in low amounts and with its products, physiologically modulates cell function. The redox state and ROS scavengers largely control the emission (generation scavenging) of $O_2(*-)$. Cell ischemia, hypoxia, or toxins can result in excess $O_2(*-)$ production when the redox state is altered and the ROS scavenger systems are overwhelmed. An initial increase in ROS can cause an even greater increase in ROS and allow excess mitochondrial $Ca^{2+}$ entry, both of which are factors that induce cell apoptosis and necrosis. The products and methods of the disclosure for the targeted biosynthesis of biocompatible noble metal nanoparticles (NPs) from a noble metal precursor salt reduce ROS or prevent the increase in ROS.

It is known, for example, that excess ROS produced can either oxidize biomolecules or can structurally modify proteins and genes so as to trigger signaling cascades that can lead to the onset and progression of chronic inflammation and inflammatory disorders. ROS-induced activation of transcription factors and pro-inflammatory genes lead to the onset of inflammation. Reflexively, an enhanced ROS generation by immune cells at the site of inflammation causes oxidative stress and tissue injury. Likewise, it is known that cumulative oxidative stress induces cellular damage, impairment of the DNA repair system, and mitochondrial dysfunction, all of which have been implicated in the development of neurodegenerative disorders. Moreover, the heart depends on continuous mitochondrial ATP supply and maintained redox balance to properly develop force, particularly under increased workload. During diabetes, however, myocardial energetic redox balance is perturbed, contributing to the systolic and diastolic dysfunction known as diabetic cardiomyopathy (DC). High glucose alters cellular redox balance and affects mitochondrial DNA (Aon et al., Antioxid. Redox Signal., 2015, 22:1563-86) and mitochondrial dysfunction contributes to heart mechanical failure. These are simply some of the multiple mechanisms in which oxidative stress causes a variety of diseases and conditions. In some aspects, the disclosure provides compositions and methods for ameliorating, treating, and/or preventing a variety of hypoxic conditions or diseases. In some aspects, some diseases associated with hypoxia and/or oxidative stress include, but are not limited to, chronic inflammation, inflammatory disorders, neurodegenerative diseases (such as, for example, Alzheimer's disease, amyotrophic lateral sclerosis (ALS), and Parkinson's disease), diabetes, cardiovascular diseases (such as, for example, high blood pressure, atherosclerosis, myocardial infarction, and stroke), chronic fatigue syndrome, asthma, chronic obstructive pulmonary disease, infertility, and cancer. The products and methods of the disclosure reduce oxidative stress which in turn is useful in ameliorating, treating, and/or preventing a variety of these hypoxic conditions or diseases.

Antioxidants are substances that neutralize or remove free radicals by donating an electron. The neutralizing effect of antioxidants helps protect the body from oxidative stress. The disclosure provides products and methods for the targeted biosynthesis of biocompatible noble metal nanoparticles (NPs) from noble metal precursors. The noble metal NPs in turn act as antioxidants by donating electrons where there are excess free radicals to restore the redox state of the cell, tissue or organ suffering oxidative stress or hypoxia. In other words, the disclosure provides products and methods for the targeted biosynthesis of biocompatible noble metal nanoparticles (NPs) which act as antioxidants by donating electrons where there are excess free radicals to increase the oxidized forms of the redox state components in the cell. The products and methods of the disclosure produce noble metal NPs which in turn restore the redox state of the cell, reduce oxidative stress and hypoxia, and are useful therefore in ameliorating, treating, and/or preventing a variety of hypoxic conditions or diseases.

A "noble metal precursor," as used herein, is a noble metal, such as gold (Au), silver (Ag), platinum (Pt), palladium (Pd), ruthenium (Ru), rhodium (Rh), osmium (Os), or iridium (Ir), or a noble metal halide, hydroxide, or a complex thereof with one or more organic ligands (e.g., biocompatible gold-thiolate complexes, such as auranofin, solganal, and monochrysine; i.e., ATP ligands), or combinations thereof. The disclosure utilizes noble metal percursors for the targeted biosynthesis of biocompatible noble metal nanoparticles (NPs) at a site of hypoxia. Noble metal NPs display strong catalytic activity, e.g., in hydrogenation, hydration, and oxidation reactions, due to their large surface area and the high proportion of metal atoms located on their surfaces (Shibuya et al., PLoS ONE 9(10):e109288. doi: 10.1371/journal.pone.0109288 (2014)). Such noble metal NP catalysts are considered to function as antioxidants (Shibuya et al. (2014), supra) and are useful in the products and methods described herein.

Noble metal NPs, as described herein, are formed in situ, at sites of hypoxia in the cell or in the vicinity of the cell in the presence of noble metal precursors. The cell, in various aspects, is in vivo, ex vivo, or in vitro. In some aspects, the noble metal precursor is a metal chloride. In some aspects, the noble metal precursor is a gold chloride. In some aspects, the gold chloride is gold monochloride (AuCl), gold dichloride ($AuCl_2$ or $Au_4Cl_8$), gold trichloride ($AuCl_3$ or $Au_2Cl_6$), or chloroauric acid ($HAuCl_4$). In some aspects, the noble metal precursor is a silver chloride. In some aspects, the silver chloride is silver monochloride (AgCl). In some aspects, the noble metal precursor is a platinum chloride. In some aspects, the platinum chloride is platinum dichloride ($PtCl_2$), platinum tetrachloride ($PtCl_4$), or hexachloroplatinic acid ($H_2PtCl_6$). In some aspects, the noble metal precursor is a palladium chloride. In some aspects, the palladium chloride is palladium dichloride ($PdCl_2$). In some aspects, the noble metal precursor is an iridium chloride. In some aspects, the iridium chloride is iridium trichloride ($IrCl_3$) or hexachloroiridic acid ($H_2IrCl_6$). In some aspects, the noble metal precursor is a ruthenium chloride. In some aspects, the ruthenium chloride is ruthenium dichloride ($RuCl_2$), or ruthenium trichloride ($RuCl_3$). In some aspects, the noble metal precursor is a rhodium chloride. In some aspects, the rhodium chloride is rhodium trichloride ($RhCl_3 (H_2O)_n$). In some aspects, the noble metal precursor is an osmium chloride. In some aspects, the osmium chloride is osmium trichloride ($OsCl_3$). Other suitable noble metal precursors include, but are not limited to, $AuF_3$, $AuBr_3$, $AuI$, $AuF_5$, $[AuCl_4]^-$, $AgF_2$, $AgF_3$, $AgF$, $AgBr$, $AgI$, $[AgF_4]^{2-}$, $[PdCl_6]^2$, $PtF_4$, $PtBr_4$, $PtI_4$, $PtBr_2$, $PtF_6$, $[PtCl_6]^{2-}$, $IrBr_3$, $IrF_3$, $IrI_3$, $IrF_4$, $Ir_4F_{20}$, $IrF_6$, $[IrCl_6]^{2-}$, $[IrCl_6]^{3-}$, $RuF_6$, $Ru_4F_{20}$, $RuF_6$, $RuBr_3$, $RuBr_2$, $RuI_2$, $RhF_6$, $RhF_4$, $RhF_5$, $[RhCl_6]^{3-}$, $OsF_6$, $OsF_5$, $OsBr_3$, $OsI_3$, $OsI_2$, $OsI$, $PdCl_2(PPh_3)_2$, $PdCl_2(NH_3)_2$, $Pt(NH_3)_2Cl_2$, $IrCl(CO)(PPh_3)_2$, $(NH_4)_3IrCl_6$, $RuOF_4$; $RuHCl(CO)(PPh_3)_3$, $RuCl_2(PPh_3)_3$, $RuHCl(PPh_3)_3$, and $(Ph_3P)_3RhCl$. Additionally, based on standard reduction potentials summarized in "A redox interaction-engaged strategy for multicomponent nanomaterials," by Wang et al. (Chem. Soc. Rev., 49, 736-764, 2020) other noble metal precursors which can be used are AgCl and other salts, such as Pd2+, Ru2+, Ru3+.

As set out above, various types of noble metal precursors are used in the disclosure to form noble metal nanoparticles. In some exemplary embodiments, such nanoparticles are gold nanoparticles. In some other embodiments, such nanoparticles are silver nanoparticles. The disclosure, however, includes the use of any type of noble metal nanoparticles, and is not limited to gold and silver nanoparticles. For example, such nanoparticles include platinum nanoparticles, which are known to have antioxidant and anti-inflammatory properties (Pedone et al, Chem Soc Rev, 46, 4951-4975, 2017).

Biosynthesis of NPs is a striking phenomenon in nature. Inspiring examples include storage and transport of iron atoms in a non-toxic form of ferric oxyhydroxide cluster in the ferritin protein cage (Seckback, J Plant Nutr, 1982, 5:369-394) using metal salts as terminal sinks in electron transfer pathways and formation of metal particles by bacteria (Caccavo et al., Appl Environ Microb, 1994, 60: 3752-3759; Methke et al., Science, 2003, 302:1967-1969) and biomineralization of magnetite nanocrystals in specific organelle magnetosome that enables coordinated movement of magnetotactic bacteria (Blakemore, Science, 1975, 190, 377-379). Under certain experimental conditions, metal complexes and nanoclusters can be obtained in mammalian cells or in a whole animal, mainly for use in imaging (Jin et al., Colloids Surf B Biointerfaces, 2018, 163, 385-393; Ye et al., Biomater Sci-Uk, 2016, 4, 652-660; Wang et al., Sci Rep-Uk, 2013, 3; Pilapong et al., Mater Lett, 2015, 140, 162-165; Gao et al., Sci Rep-Uk, 2014, 4; Chen et al., Acs Appl Mater Inter, 2015, 7, 18163-18169; Fernandez et al., Biomaterials, 2015, 43, 1-12). However, the mechanisms of these biosyntheses are often spontaneous, poorly understood and, therefore, difficult to control. In the products and methods of the disclosure, a pathological process initiates and controls biosynthesis of biocompatible noble metal nanoparticles, e.g., gold NPs, from noble metal precursor salts (a gold chloride) in the immediate vicinity of the hypoxia site, thereby restoring the redox state of the brain.

The products and methods described herein utilize a strong electron donating ability of reduced electron donors from redox couples, such as NADH cofactor, NADPH, GSH, and $TrxSH_2$, to drive biosynthesis of noble metal NPs, e.g., gold NPs, from a corresponding noble metal precursor in situ in cells, tissues, and organs under hypoxia conditions, such as the living brain, as depicted in FIG. 1A. An excess of reducing equivalents accumulate near a site of hypoxia, and these reducing equivalents can be redirected to the metal ion reduction reaction, while the formed oxidized NAD+ became available to serve as a strong electron sink to restore the normal physiological NADH/NAD+ ratio and cellular respiration, and ultimately help protect the brain. Noble metal-based nanostructures, such as gold NPs, are very appealing for biomedical applications owing to their high biocompatibility and in vivo stability (Farooq et al., 2018, Sci Rep-Uk, 8; Giljohann et al., Angew Chem Int Edit, 2010, 49:3280-94; Murphy et al., Accounts Chem Res, 2008, 41:1721-30; Thakor et al., Nano Lett, 2011, 11:4029-36). Moreover, the inherent antioxidant properties of Au NPs (Valgimigli, et al., J Mater Chem B, 2018, 6:2036-51) as various ROS scavengers (Esumi et al., Colloid Surface B, 2003, 32:117-23; He et al., Biomaterials, 2013, 34: 765-73; Li et al., Biomaterials, 2015, 48: 37-44) add remarkable value to their tissue's protection potential.

Nicotinamide adenine dinucleotide (NAD) is a cofactor that is central to metabolism. Found in all living cells, NAD is called a dinucleotide because it consists of two nucleotides joined through their phosphate groups. One nucleotide contains an adenine nucleobase and the other nicotinamide. NAD exists in two forms: an oxidized and reduced form, abbreviated as NAD+ and NADH respectively. In metabolism, NAD is involved in redox reactions, carrying electrons from one reaction to another. The cofactor is, therefore, found in two forms in cells: NAD+ is an oxidizing agent—it accepts electrons from other molecules and becomes reduced. This reaction forms NADH, which can then be used as a reducing agent to donate electrons. In various aspects of the disclosure, a noble metal precursor is transformed into a noble metal nanoparticle and NAD in the presence of the reducing agent, NADH, at a site of hypoxia. In other words, NADH serves as the electron donor (i.e., the H in the NADH) for oxidation of NADH to NAD$^+$, changing the redox ratio by increasing the ratio of NAD$^+$/NADH or decreasing the ratio of NADH/NAD+ at the site of hypoxia.

Nicotinamide adenine dinucleotide phosphate (NADPH) is the reduced form of NADP+ (nicotinamide adenine dinucleotide phosphate), an important cofactor used in anabolic reactions in all forms of cellular life. NADP+ differs from NAD+ in the presence of an additional phosphate group on the 2' position of the ribose ring that carries the adenine moiety. This extra phosphate is added by NAD+ kinase and removed by NADP+ phosphatase. NADPH is produced from NADP+. The major source of NADPH in animals and other non-photosynthetic organisms is the pentose phosphate pathway, by glucose-6-phosphate dehydrogenase (G6PDH) in the first step. The pentose phosphate pathway also produces pentose, another important part of NAD(P)H, from glucose. NADPH provides the reducing equivalents for biosynthetic reactions and the oxidation-reduction involved in protecting against the toxicity of ROS, allowing the regeneration of glutathione (GSH). NADPH is also used for anabolic pathways, such as cholesterol synthesis and fatty acid chain elongation. The NADPH system is responsible for generating free radicals in immune cells by NADPH oxidase. These radicals are used to destroy pathogens in a process termed the respiratory burst. Thus, in various aspects of the disclosure, a noble metal precursor is transformed into a noble metal nanoparticle and NADP in the presence of the reducing agent, NADPH, at a site of hypoxia. In other words, NADPH serves as the electron donor (i.e., the H in the NADPH) for oxidation of NADPH to NADP$^+$, changing the redox ratio by increasing the ratio of NADP$^+$/NADH or decreasing the ratio of NADH/NADP+ at the site of hypoxia.

Glutathione (GSH) is a tripeptide that contains L-cysteine, L-glutamic acid and glycine. It is the smallest intracellular protein thiol molecule in the cells, which prevents cell damage caused by reactive oxygen species such as free radicals and peroxides. Glutathione exists in reduced (GSH) and oxidized (GSSG) states. The plasma GSH/GSSG ratio seems to play a major role in the modulation of glucose homeostasis mainly in diabetics. Reduced glutathione (GSH) is a major tissue antioxidant that provides reducing equivalents for the glutathione peroxidase (GPx) catalyzed reduction of lipid hydroperoxides to their corresponding alcohols and hydrogen peroxide to water. In the GPx catalyzed reaction, the formation of a disulfide bond between two GSH molecules generates oxidized glutathione (GSSG). Glutathione reductase (GR) recycles GSSG to GSH with the simultaneous oxidation of β-nicotinamide adenine dinucleotide phosphate (β-NADPH2). Thus, in various aspects of the disclosure, a noble metal precursor is transformed into a noble metal nanoparticle and GSSG in the presence of the reducing agent, GSH, at the site of hypoxia. In other words, GSH serves as the electron donor for oxidation of GSH to GSSG, changing the redox ratio by increasing the ratio of GSSG/GSH or decreasing the ratio of GSH/GSSG at the site of hypoxia.

The glutathione peroxidase/glutathione reductase system removes $H_2O_2$ using GSH as an electron source, and the thioredoxin peroxidase/thioredoxin reductase system uses electrons from reduced thioredoxin (TrxSH$_2$) to convert a noble metal precursor to a noble metal nanoparticle and oxidized thioredoxin (TrxSS). Thus, in various aspects of the disclosure, a noble metal precursor is transformed into a noble metal nanoparticle and TrxSS in the presence of the reducing agent, TrxSH$_2$, at the site of hypoxia. In other words, TrxSH$_2$ serves as the electron donor for oxidation of TrxSH$_2$ to TrxSS, changing the redox ratio by increasing the ratio of TrxSS/TrxSH$_2$ or decreasing the ratio of TrxSH$_2$/Trxss at the site of hypoxia.

The disclosure therefore provides a noble metal precursor as described herein. The disclosure also provides a combination of two or more of the noble metal precursors described herein. The disclosure also provides a composition comprising a noble metal precursor or the combination of two or more noble metal precursors as described herein. In some aspects, the composition is a pharmaceutical composition. As used herein, the term "pharmaceutical composition" relates to a composition which is suitable for administration to a subject. In some aspects, the subject is a mammal. In some aspects, the mammal is a human. In some aspects, the composition comprises a noble metal precursor, or a combination thereof, preferably in a diagnostically effective amount. In some aspects, the pharmaceutical composition comprises a noble metal precursor, or a combination thereof, preferably in a therapeutically effective amount. In some aspects, the composition or pharmaceutical composition further comprises suitable formulations of one or more (pharmaceutically effective) carriers, stabilizers, excipients, diluents, solubilizers, surfactants, emulsifiers, preservatives and/or adjuvants. Acceptable constituents of the composition are preferably nontoxic to recipients at the dosages and concentrations employed. Pharmaceutical compositions of the invention include, but are not limited to, liquid, frozen, and lyophilized compositions.

In some aspects, the composition comprises a pharmaceutically acceptable carrier. In general, as used herein, "pharmaceutically acceptable carrier" means any and all aqueous and non-aqueous solutions, sterile solutions, solvents, buffers, e.g. phosphate buffered saline (PBS) solutions, water, suspensions, emulsions, such as oil/water emulsions, various types of wetting agents, liposomes, dispersion media and coatings, which are compatible with pharmaceutical administration, in particular with parenteral administration. The use of such carriers in pharmaceutical compositions is well known in the art, and the compositions comprising such carriers, in various aspects, are formulated by well-known conventional methods.

Some embodiments provide pharmaceutical compositions comprising the noble metal precursors and further one or more excipients such as those illustratively described in this section and elsewhere herein. Excipients, in some aspects, are used for a wide variety of purposes, such as adjusting physical, chemical, or biological properties of formulations, such as adjustment of viscosity, and or processes of the invention to improve effectiveness and or to stabilize such formulations and processes against degradation and spoilage due to, for instance, stresses that occur during manufacturing, shipping, storage, pre-use preparation, administration, and thereafter.

In some embodiments, the pharmaceutical composition may contain formulation materials for the purpose of modifying, maintaining or preserving, e.g., the pH, osmolarity, viscosity, clarity, color, isotonicity, odor, sterility, stability, rate of dissolution or release, adsorption or penetration of the composition (see, REMINGTON'S PHARMACEUTICAL SCIENCES, 18" Edition, (A. R. Genrmo, ed.), 1990, Mack Publishing Company). In such embodiments, suitable formulation materials may include, but are not limited to:

amino acids such as glycine, alanine, glutamine, asparagine, threonine, proline, 2-phenylalanine, including charged amino acids, preferably lysine, lysine acetate, arginine, glutamate and/or histidine
antimicrobials such as antibacterial and antifungal agents
antioxidants such as ascorbic acid, methionine, sodium sulfite or sodium hydrogen-sulfite;
buffers, buffer systems and buffering agents which are used to maintain the composition at physiological pH or at a slightly lower pH, preferably a lower pH of 4.0 to 6.5; examples of buffers are borate, bicarbonate, Tris-HCl, citrates, phosphates or other organic acids, succinate, phosphate, and histidine; for example Tris buffer of about pH 7.0-8.5;
non-aqueous solvents such as propylene glycol, polyethylene glycol, vegetable oils such as olive oil, and injectable organic esters such as ethyl oleate;
aqueous carriers including water, alcoholic/aqueous solutions, emulsions or suspensions, including saline and buffered media;
biodegradable polymers such as polyesters;
bulking agents such as mannitol or glycine;
chelating agents such as ethylenediamine tetraacetic acid (EDTA);
isotonic and absorption delaying agents;
complexing agents such as caffeine, polyvinylpyrrolidone, beta-cyclodextrin or hydroxypropyl-beta-cyclodextrin)
fillers;
monosaccharides; disaccharides; and other carbohydrates (such as glucose, mannose or dextrins); carbohydrates may be non-reducing sugars, preferably trehalose, sucrose, octasulfate, sorbitol or xylitol;
(low molecular weight) proteins, polypeptides or proteinaceous carriers such as human or bovine serum albumin, gelatin or immunoglobulins, preferably of human origin;
coloring and flavouring agents;
sulfur containing reducing agents, such as glutathione, thioctic acid, sodium thioglycolate, thioglycerol, [alpha]-monothioglycerol, and sodium thio sulfate
diluting agents;
emulsifying agents;
hydrophilic polymers such as polyvinylpyrrolidone)
salt-forming counter-ions such as sodium;
preservatives such as antimicrobials, anti-oxidants, chelating agents, inert gases and the like; examples are: benzalkonium chloride, benzoic acid, salicylic acid, thimerosal, phenethyl alcohol, methylparaben, propylparaben, chlorhexidine, sorbic acid or hydrogen peroxide);
metal complexes such as Zn-protein complexes;
solvents and co-solvents (such as glycerin, propylene glycol or polyethylene glycol);
sugars and sugar alcohols, such as trehalose, sucrose, octasulfate, mannitol, sorbitol or xylitol stachyose, mannose, sorbose, xylose, ribose, myoinisitose, galactose, lactitol, ribitol, myoinisitol, galactitol, glycerol, cyclitols (e.g., inositol), polyethylene glycol; and polyhydric sugar alcohols;
suspending agents;
surfactants or wetting agents such as pluronics, PEG, sorbitan esters, polysorbates such as polysorbate 20, polysorbate, triton, tromethamine, lecithin, cholesterol, tyloxapal; surfactants may be detergents, preferably with a molecular weight of >1.2 KD and/or a polyether, preferably with a molecular weight of >3 KD; non-limiting examples for preferred detergents are Tween 20, Tween 40, Tween 60, Tween 80 and Tween 85; non-limiting examples for preferred polyethers are PEG 3000, PEG 3350, PEG 4000 and PEG 5000;
stability enhancing agents such as sucrose or sorbitol;
tonicity enhancing agents such as alkali metal halides, preferably sodium or potassium chloride, mannitol sorbitol;
parenteral delivery vehicles including sodium chloride solution, Ringer's dextrose, dextrose and sodium chloride, lactated Ringer's, or fixed oils;
intravenous delivery vehicles including fluid and nutrient replenishers, electrolyte replenishers (such as those based on Ringer's dextrose).

In some aspects, a pharmaceutical composition, is a liquid composition, a solid composition obtained by lyophilisation, or a reconstituted liquid composition.

It is envisaged that the composition of the disclosure may comprise, in addition to the noble metal precursor described herein, further biologically active agents, depending on the intended use of the composition. Such agents may be drugs acting on the various organs or systems the noble metal precursor is intended to target. It is also envisaged that the noble metal precursor is applied in a co-therapy, i.e., in combination with another drug, agent, or medicament.

In some embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the noble metal precursor. In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In certain embodiments, the noble metal precursor composition is prepared for storage by mixing the selected composition with optional formulation agents (REMINGTON'S PHARMACEUTICAL SCIENCES, supra) in the form of a lyophilized cake or an aqueous solution. Further, in certain embodiments, the noble metal precursor composition is formulated as a lyophilizate using appropriate excipients such as sucrose.

When parenteral administration is contemplated, the composition of the disclosure is provided in the form of a pyrogen-free, parenterally acceptable aqueous solution comprising the desired noble metal precursor in a pharmaceutically acceptable vehicle. A particularly suitable vehicle for parenteral injection is sterile distilled water in which the noble metal precursor is formulated as a sterile, isotonic solution, properly preserved. In certain embodiments, the noble metal precursor is formulated with an agent, such as injectable microspheres, bio-erodible particles, polymeric compounds (such as polylactic acid or polyglycolic acid), beads, micelles, and/or liposomes, that may provide controlled or sustained release of the product which can be delivered via depot injection. In certain embodiments, hyaluronic acid or PEG may also be used, having the effect of promoting sustained duration in the circulation.

Additional compositions or pharmaceutical compositions will be evident to those skilled in the art, including formulations involving the noble metal precursor composition in sustained- or controlled-delivery/release formulations. Techniques for formulating a variety of other sustained- or controlled-delivery means, such as liposome or micelle carriers, bio-erodible microparticles or porous beads and depot injections, are also known to those skilled in the art. Sustained-release preparations may include semipermeable polymer matrices in the form of shaped articles, e.g., films, or microcapsules. Sustained release matrices may include polyesters, hydrogels, polylactides, copolymers of L-glutamic acid and gamma ethyl-L-glutamate, poly (2-hydroxyethyl-methacrylate), ethylene vinyl acetate or poly-D(-)-3-hydroxybutyric acid. Sustained release compositions may also include liposomes that can be prepared by any of several methods known in the art.

Pharmaceutical compositions used for in vivo administration are typically provided as sterile preparations. Sterilization can be accomplished by filtration through sterile filtration membranes. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

In some aspects, the composition may further comprise a salt, a surfactant, an antioxidant, or a preservative. Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration.

The formulations described herein are useful as pharmaceutical compositions in the treatment, amelioration and/or prevention of the medical condition as described herein in a subject in need thereof. The term "treatment" refers to both therapeutic treatment and prophylactic or preventative measures. Treatment includes the application or administration of the formulation to the body, an isolated tissue, or cell from a patient who has a disease/disorder, a symptom of a disease/disorder, or a predisposition toward a disease/disorder, with the purpose to cure, heal, alleviate, relieve, alter, remedy, ameliorate, improve, or affect the disease, the symptom of the disease, or the predisposition toward the disease.

In some aspects, the disclosure provides a changing the oxidation-reduction (redox) state of a cell undergoing or at risk of undergoing hypoxia comprising administering to the cell a noble metal precursor. In the cell, or in the vicinity of the cell, due to the permeability of the cell membrane to small molecules, the noble metal precursor is converted to a biocompatible antioxidant noble nanoparticle and the redox ratio of NAD+/NADH, NADP+/NADPH, GSSG/GSH, or TrxSS/TrxSH$_2$ is increased. The products and methods described herein utilize a strong electron donating ability of reduced electron donors from redox couples, such as NADH cofactor, NADPH, GSH, and TrxSH$_2$, to drive biosynthesis of the biocompatible antioxidant noble metal NPs from a corresponding noble metal precursor in situ in cells, tissues, and organs that are undergoing hypoxic conditions. The noble metal NPs can remain at the site of the cells in the tissue or organ susceptible or at risk of hypoxic conditions to maintain the redox state and to prevent hypoxic damage.

The term "amelioration" as used herein refers to any improvement of the condition or disease state of a subject as specified herein below, by the administration of the noble metal precursor or a composition comprising the same to a subject in need thereof. Such an improvement may also be seen as a slowing or stopping of the progression of the condition or disease of the subject. The term "prevention" as used herein means the avoidance of the occurrence or re-occurrence of the condition or disease in the subject as specified herein below, by the administration of the noble metal precursor or a composition comprising the same to a subject in need thereof.

The term "disease" or "disorder" refers to any condition that would benefit from treatment with the noble metal precursor or the composition comprising the same described herein. This includes chronic and acute diseases or disorders including those pathological conditions that predispose the subject to the disease at issue. In some aspects, the condition, disease, or disorder is one which would benefit from normalization of an oxidation-reduction (redox) state of a cell, tissue, and/or organ undergoing or at risk of undergoing hypoxia.

Thus, in some aspects, the disclosure provides a method for preventing, treating, or ameliorating hypoxia in a cell, tissue or organ suffering from or at risk of suffering from hypoxia. Hypoxia is a condition or state in which the supply of oxygen is insufficient for normal life functions. The body or a region of the body is deprived of adequate oxygen supply at the cell and/or tissue level. Hypoxia may be classified as either generalized, affecting the whole body, or local, affecting a region of the body. Although hypoxia is often a pathological condition, variations in arterial oxygen concentrations can be part of the normal physiology, for example, during hypoventilation training or strenuous physical exercise. In severe hypoxia, or hypoxia of very rapid onset, ataxia, confusion, disorientation, hallucinations, behavioral change, severe headaches, reduced level of consciousness, papilloedema, breathlessness, pallor, tachycardia, and pulmonary hypertension eventually leading to the late signs cyanosis, slow heart rate and low blood pressure, followed by heart failure eventually leading to shock and death. In some aspects, ischemia, or insufficient blood flow to a tissue, can also result in hypoxia. This is called ischemic hypoxia. In some aspects, hypoxemic hypoxia, is a hypoxic condition wherein the arterial content of oxygen is insufficient. As used herein, the term "hypoxia" encompasses all of these conditions or states and the products and methods described herein are used in treating these conditions.

In some aspects, a cell, tissue, or organ is in a state of hypoxia resulting from oxidative stress, oxygen free radical damage, or ischemia-reperfusion injury. "Oxidative stress" is an imbalance between free radicals and antioxidants in the body, which can lead to cell and tissue damage called "oxygen free radical damage." Oxidative stress also occurs naturally and plays a role in the aging process. "Ischemia-reperfusion injury" of "IRI" represents a pathological condition characterized by an initial undersupply of blood to an area or organ followed by a restoration of perfusion and concomitant reoxygenation (=reperfusion). Ischemia typically occurs in the presence of embolism or thrombosis but can also be triggered by surgery and transplantation. The disturbance in perfusion results in a severe imbalance between metabolic supply and demand, subsequently causing tissue hypoxia. All tissues and organs are susceptible to ischemia, but susceptibility to an ischemic insult differs between organ systems. Restoration of blood flow and reoxygenation, however, is commonly associated with an exacerbation of tissue injury and a profound inflammatory response. Such IRI contributes to pathology in a wide range of conditions. For example, myocardial ischemia followed by reperfusion typically manifests in microvascular dysfunction, death of myocytes, and myocardial stunning or dysfunction. IRI of the lung, for example, following transplantation, is characterized by nonspecific alveolar damage, edema formation, and hypoxemia. The clinical spectrum of pulmonary IRI may range from mild hypoxemia to acute respiratory distress syndrome. In contrast to other organs, the brain is particularly susceptible to ischemia and irreversible neuronal damage already occurs after only five minutes of complete ischemia. For brain ischemia, as occurring in the setting of stroke, reestablishing reperfusion seems to be only beneficial, if carried out within a short time period after the onset of ischemia. Reperfusion of ischemic stroke seems to be very critical, as patients may suffer from cerebral reperfusion injury manifesting in fatal cerebral edema formation and intracranial hemorrhage. IRI of the kidney may occur in the setting of transplantation and cardiac arrest and during cardiac surgery. Here it is important to note that renal injury is usually associated with a high morbidity and mortality. The cortical-medullary region is the most susceptible region to tubular injury, inflammation, and vascular alterations. Generally, IRI of a single organ causes the release of different proinflammatory mediators, which may subsequently induce inflammation in other organs, thereby potentially contributing to multiple organ dysfunction or even failure. The disclosure includes products and methods for treating, ameliorating or preventing such oxidative stress, oxygen free radical damage, and ischemia-reperfusion injuries.

In some aspects, the cell, tissue or organ suffering from or at risk of suffering from hypoxia is the result of a hypoxia-related disease or disorder. In some aspects, such disease or disorder includes, but is not limited to, chronic inflammation, inflammatory disorders, neurodegenerative diseases (such as, for example, Alzheimer's disease, amyotrophic lateral sclerosis (ALS), and Parkinson's disease), retinal disease, hyperglycemia, diabetes, thrombosis, cardiovascular diseases (such as, for example, high blood pressure, atherosclerosis, myocardial infarction, and stroke), chronic fatigue syndrome, asthma, chronic obstructive pulmonary disease, infertility, ulcer, bacterial infection, sepsis, gangrene and cancer. In some aspects, the products and methods described herein are particularly advantageous for the therapy of cancer. In some aspects, the products and methods described herein are used in the treatment of solid tumors. In some aspects, the products and methods described herein are advantageous in the treatment of carcinomas. In some aspects, the cancer includes, but is not limited to, prostate cancer, breast cancer, skin cancer, lung cancer, pancreatic cancer, stomach cancer, intestinal cancer, kidney cancer, liver cancer, retinal cancer, brain cancer, bone cancer, thyroid cancer, head and neck cancer, cervical cancer, uterine cancer, anal cancer, and other cancers involving other glands and organs. In some aspects, the products and methods described herein are used in the treatment of any cancer that is treatable via thermotherapy or hyperthermia, especially since in situ formed photonic NPs can be heated using laser.

In some aspects, the cell, tissue or organ suffering from or at risk of suffering from hypoxia is the result of aging. Skin aging induced by chronological or intrinsic factors leads to skin atrophy. The amounts of skin collagen components fall in an age-dependent manner in both males and females, resulting in age-related skin thinning in older individuals. Evidence suggests that oxidatively modified proteins, DNA, and lipids in the skin and other organs progressively accumulate during aging, indicating that reactive oxygen species (ROS) are strongly associated with skin aging and other various aging-related organ phenotypes, such as age-related macular degeneration, fatty deposits in the liver, skin atrophy, bone loss and fragility, progression of Alzheimer's disease, infertility, dry eye, and rotator cuff degeneration. These findings suggest that oxidative damage is the primary cause of aging-related changes in various tissues (Shibuya et al., PLoS ONE 9(10):e109288. doi:10.1371/journal.pone.0109288). The disclosure includes products and methods for treating, ameliorating or preventing such aging conditions resulting from oxidative stress or damage.

The terms "subject," "subject in need" or those "in need of treatment" includes those already suffering from the disorder, as well as those in which the disorder is to be prevented. The subject in need includes human and other mammalian subjects that receive either prophylactic or therapeutic treatment.

In some aspects, the disclosure provides products and methods for screening drugs or other therapeutics for their antioxidant activity. Thus, in some aspects, a noble metal precursor is administered to a cell or cell culture in vitro, or is administered to a cell, tissue, or organ of a subject in vivo, in the presence of a candidate drug or therapeutic to determine if or how the candidate drug or therapeutic affects the redox state and the rate of formation of the noble metal nanoparticles. In other words, the disclosure provides products and methods for observing the targeted biosynthesis or the rate of the targeted biosynthesis of biocompatible noble metal nanoparticles (NPs) which act as antioxidants by donating electrons where there are excess free radicals to increase the oxidized forms of the redox state components in the cell. These products and methods are useful in determining the efficacy of various drugs or therapeutics.

The methods of the disclosure, in various aspects, can be applied in drug or quality screening. For example, in the pharmaceutical industry, many efforts are directed towards the development of synthetic drugs to control specific factors involved in the cellular response to hypoxia (for example, to reduce gene expression or inhibit hypoxia-inducible factor (HIF) prolyl hydroxylase or to induce the expression of nuclear factor erythroid 2-related factor 2 (NRF2), both of which regulates the expression of antioxidant proteins that protect against oxidative damage triggered by injury and inflammation. The efficacy of combinatorial drug candidate pools can be rapid tested on microtissue or cell models under hypoxic conditions in the presence of Au NPs precursor salts. In these test systems, the appearance of NPs (for example, in some applications observed as a color change) serve as a marker of a certain level of hypoxia and/or the conversion of noble metal precursors to noble metal NPs. Thus, the increase or decrease in expression of the marker is used to measure the effectiveness of the drug or agent as an anti-hypoxic agent.

The noble metal precursor or composition comprising the noble metal precursor will generally be designed for specific routes and methods of administration, for specific dosages and frequencies of administration, for specific treatments of specific diseases, with ranges of bio-availability and persistence, among other things. The materials of the composition are preferably formulated in concentrations that are acceptable for the site of administration.

Formulations and compositions thus may be designed for delivery by any suitable route of administration. In the context of the disclosure, the routes of administration include, but are not limited to topical routes (such as epicutaneous, inhalational, intranasal, opthalmic, auricular/aural, vaginal, mucosal);

enteral routes (such as oral, gastrointestinal, sublingual, sublabial, buccal, rectal); and parenteral routes (such as intravenous, intraarterial, intraosseous, intramuscular, intracerebral, intracerebroventricular, intracisternal, epidural, intrathecal, subcutaneous, intraperitoneal, extra-amniotic, intraarticular, intracardiac, intradermal, intralesional, intrauterine, intravesical, intravitreal, transdermal, intranasal, transmucosal, intrasynovial, and intraluminal).

The compositions delivered by injection may be delivered in a bolus injection or by infusion, such as continuous infusion. Likewise, the compositions may be administered using a medical device. The continuous or uninterrupted administration of the composition may be intravenous or subcutaneous by way of a fluid delivery device or small pump system including a fluid driving mechanism for driving fluid out of a reservoir and an actuating mechanism for actuating the driving mechanism. Pump systems for subcutaneous administration may include a needle or a cannula for penetrating the skin of a patient and delivering the suitable composition into the patient's body. Said pump systems may be directly fixed or attached to the skin of the patient independently of a vein, artery or blood vessel, thereby allowing a direct contact between the pump system and the skin of the subject.

The continuous administration may also be transdermal by way of a patch worn on the skin and replaced at intervals. One of skill in the art is aware of patch systems for drug delivery suitable for this purpose. It is of note that transdermal administration is especially amenable to uninterrupted administration, as exchange of a first exhausted patch can advantageously be accomplished simultaneously with the placement of a new, second patch, for example on the surface of the skin immediately adjacent to the first exhausted patch and immediately prior to removal of the first exhausted patch. Issues of flow interruption or power cell failure do not arise.

In some aspects, a composition of the disclosure is delivered to the subject at a suitable dose which can be determined, for example, by dose escalating studies by administration of increasing doses of the noble metal precursor. The dosage regimen will be determined by the attending physician and clinical factors. As is well known in the medical arts, dosages for any one subject depends upon many factors, including the patient's size, body surface area, age, the compound to be administered, sex, time and route of administration, general health, and other drugs being administered concurrently.

The term "effective dose" or "effective dosage" is defined as an amount sufficient to achieve or at least partially achieve the desired effect. The term "therapeutically effective dose" is defined as an amount sufficient to cure or at least partially ameliorate the disorder or disease and its complications in a subject suffering therefrom. Amounts or doses effective for this use will depend on the condition to be treated (the indication), the noble metal precursor, the therapeutic context and objectives, the severity of the condition, disorder, or disease, prior therapy, the subject's clinical history and response, the route of administration, the size (body weight, body surface or organ size) and/or condition (the age and general health) of the subject, and the general state of the subject. The proper dose can be adjusted according to the judgment of the attending physician such that it can be administered to the subject once or over a series of administrations, and in order to obtain the desired or optimal therapeutic effect.

In some aspects, a typical dosage, effective amount, or therapeutic effective amount may range from about 0.1 pmol/g to about 1 mol/g. Thus, in some aspects the dose is about 0.1 pmol/g, about 1 pmol/g, about 10 pmol/g, about 100 pmol/g, about 1 nmol/g, about 10 nmol/g, about 100 nmol/g, about 1 µmol/g, about 10 µmol/g, about 100 µmol/g, about 1 mmol/g, about 10 mmol/g, about 100 mmol/g, or about 1 mol/g. In some aspects, the dose may range from about 0.01 µmol/g to about 100 µmol/g. In some aspects, the dose is about 0.01 µmol/g, 0.05 µmol/g, about 0.1 µmol/g, about 0.5 µmol/g, about 1.0 µmol/g, about 5.0 µmol/g, about 10 µmol/g, about 15 µmol/g, about 20 µmol/g, about 25 µmol/g, about 30 µmol/g, about 35 µmol/g, about 40 µmol/g, about 45 µmol/g, about 50 µmol/g, about 55 µmol/g, about 60 µmol/g, about 65 µmol/g, about 70 µmol/g, about 75 µmol/g, about 80 µmol/g, about 85 µmol/g, about 90 µmol/g, about 95 µmol/g, or about 100 µmol/g. In some aspects, the dose is per gram of body weight, per gram of cells, or per gram of tissue. In various aspects, a clinician will optimize the dose for the particular therapy and taking into account the particular conditions of the subject.

In some aspects of the disclosure, the noble metal precursor is administered at a concentration rather than a dose. In such instances, the concentration may range from about 1 nm to about 1 M, depending on the method. In some aspects, the concentration may range from about 1 µM to about 100 mM. In some aspects, the concentration may range from about 100 µM to about 10 mM. In some aspects, the concentration is about 1 nm, about 10 nm, about 100 nm, about 1 µM, about 10 µM, about 20 µM, about 30 µM, about 40 µM, about 50 µM, about 60 µM, about 70 µM, about 80 µM, about 90 µM, about 100 µM, about 150 µM, about 200 µM, about 250 µM, about 300 µM, about 350 µM, about 400 µM, about 450 µM, about 500 µM, about 550 µM, about 600 µM, about 650 µM, about 700 µM, about 750 µM, about 800 µM, about 850 µM, about 900 µM, about 950 µM, about 1 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 200 mM, about 300 mM, about 400 mM, about 500 mM, about 600 mM, about 700 mM, about 800 mM, about 900 mM, or about 1 M.

A therapeutic effective amount of the noble metal precursor preferably results in a decrease in severity of the condition or disease symptoms, an increase in frequency or duration of disease symptom-free periods, or a prevention of impairment or disability due to the condition or disease affliction. Thus, in some instances, a therapeutically effective amount of a composition of the disclosure, preferably reduces or inhibits hypoxia by at least about 10%, at least about 20%, at least about 30%, at least about 40%, at least about 50%, at least about 60%, at least about 70%, at least about 80%, or at least about 90% relative to untreated subjects. The ability of a compound to reduce or inhibit hypoxia may be evaluated in an in vitro model or in an in vivo animal model predictive of efficacy.

The composition, in various aspects, is administered as a sole therapeutic or in combination with additional therapies. These drugs may be administered simultaneously with the composition comprising the noble metal precursor or separately before or after administration of the noble metal precursor in timely defined intervals and doses.

The term "effective and non-toxic dose" as used herein refers to a tolerable dose of the noble metal precursor which is high enough to increase the redox ratio of the cell or cells in the target tissue and/or organ. Such effective and non-toxic doses may be determined, for example, by dose escalation studies described in the art and should be below the dose inducing severe adverse side events (dose limiting toxicity (DLT)).

The term "toxicity" as used herein refers to the toxic effects of a drug manifested in adverse events or severe adverse events. These side events may refer to a lack of tolerability of the drug in general and/or a lack of local tolerance after administration. Toxicity could also include teratogenic or carcinogenic effects caused by the drug.

The term "safety", "in vivo safety" or "tolerability" as used herein defines the administration of a drug without inducing severe adverse events directly after administration (local tolerance) and during a longer period of application of the drug. "Safety", "in vivo safety" or "tolerability" can be evaluated, for example, at regular intervals during the treatment and follow-up period. Measurements include clinical evaluation, for example, organ manifestations, and screening of laboratory abnormalities. Clinical evaluation may be carried out and deviations to normal findings recorded/coded according to NCI-CTC and/or MedDRA standards. Organ manifestations may include criteria such as allergy/immunology, blood/bone marrow, cardiac arrhythmia, coagulation and the like, as set forth e.g. in the Common Terminology Criteria for adverse events v 3.0 (CTCAE). Laboratory parameters which may be tested include for instance hematology, clinical chemistry, coagulation profile and urine analysis and examination of other body fluids such as serum, plasma, lymphoid or spinal fluid, liquor and the like. Safety can thus be assessed e.g. by physical examination, imaging techniques (i.e. ultrasound, x-ray, CT scans, Magnetic Resonance Imaging (MRI), other measures with technical devices (i.e. electrocardiogram), vital signs, by measuring laboratory parameters and recording adverse events. For example, adverse events in animals in the uses and methods of the disclosure may be examined by histopathological and/or histochemical methods.

The above terms are also referred to, for example, in the Preclinical safety evaluation of biotechnology-derived pharmaceuticals S6; ICH Harmonised Tripartite Guideline; ICH Steering Committee meeting on Jul. 16, 1997.

In some aspects, the disclosure includes a kit comprising the noble metal precursor and/or a composition comprising the same. In the context of the disclosure, the term "kit" means two or more components—one of which corresponding to the noble metal precursor or a composition comprising the same—packaged together in a type of recipient designed to hold the noble metal precursor or composition comprising the same. In some aspects, a kit is described as a set of products and/or utensils that are sufficient to achieve a certain goal, which can be marketed as a single unit.

In various aspects, the kit comprises one or more recipients (such as vials, ampoules, containers, syringes, bottles, and bags) of any appropriate shape, size and material (preferably waterproof, e.g. plastic or glass) containing the noble metal precursor or composition comprising the same in an appropriate dosage for administration (see above). The kit may additionally contain directions for use (e.g. in the form of a leaflet or instruction manual), means for administering the noble metal precursor or composition comprising the same, such as a syringe, pump, infuser or the like, means for reconstituting the noble metal precursor or composition comprising the same, and/or means for diluting the noble metal precursor or composition comprising the same.

The disclosure also provides kits for a single-dose administration unit. The kit of the disclosure may also contain a first recipient comprising the noble metal precursor and a second recipient comprising an aqueous formulation to deliver the noble metal precursor. In certain embodiments, kits containing single-chambered and multi-chambered pre-filled syringes (e.g., liquid syringes and lyosyringes) are provided.

It is noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments described herein. Such equivalents are intended to be encompassed by the disclosure.

The term "about" or "approximately" as used herein means within 20%, preferably within 10%, and more preferably within 5% of a given value or range. It includes, however, also the concrete number, for example, "about 10" includes 10.

Throughout this specification and the claims which follow, unless the context requires otherwise, the word "comprise," and variations such as "comprises" and "comprising," will be understood to imply the inclusion of a stated integer or step or group of integers or steps but not the exclusion of any other integer or step or group of integer or step. When used herein, "consisting essentially of" does not exclude materials or steps that do not materially affect the basic and novel characteristics of the claim. When used herein "consisting of" excludes any material, element, or step not specified in the claim. In each instance herein any of the terms "comprising", "consisting essentially of" and "consisting of" may be replaced with either of the other two terms.

It should be understood that the disclosure is not limited to the particular methodology, protocols, material, reagents, and substances, and the like, described herein and as such can vary. The terminology used herein is for the purpose of describing particular embodiments only, and is not intended to limit the scope of the disclosure, which is defined by the claims.

All publications and patents cited throughout the text of this specification (including all patents, patent applications, scientific publications, manufacturer's specifications, instructions, and the like), whether supra or infra, are hereby incorporated by reference in their entirety. To the extent the material incorporated by reference contradicts or is inconsistent with this specification, the specification will supersede any such material.

A better understanding of the disclosure will be obtained from the following examples, offered for illustrative purposes only. The examples are not intended to limit the scope of the disclosure.

EXAMPLES

Aspects and embodiments of the disclosure are illustrated by the following examples, which are not in any way meant to limit the scope of the invention.

Example 1

Materials and Methods

Reagents

Gold (III) chloride ($AuCl_3$) and cofactors, NADH, NADPH and ATP, were purchased from Sigma/Aldrich (St.

Louis, MO). Paraformaldehyde/glutaraldehyde fixative solution was purchased from Electron Microscopy Sciences (Hatfield, PA). Gold NPS were formed through reduction of the $AuCl_3$ by cofactors. Briefly, 100 μM NADH solution in PBS, pH 7.4, was placed in a cuvette and mixed with aliquots of $AuCl_3$ in the same buffer to achieve 4:1, 2:1, and equimolar NADH/precursor ratios, at room temperature under constant stirring. Oxidation of NADH and formation of Au NPs were recorded at 340 nm and 520 nm, respectively, by UV-vis spectra using CARY-50 spectrophotometer.

Experimental Hypoxia in Living Acute Brain Sections

All animal procedures and the brain slice preparation procedures were performed in accordance with the Institutional Animal Care and Use Committee at the University of Chicago. Experimental mice C57BL/6J (male, 17 days old, n=2) were anesthetized by intraperitoneal injection of ketamine-xylazine, decapitated, and had their brains quickly removed. The brains were placed to the ice-cold "cut" artificial cerebrospinal fluid (ACSF) solution (containing the following, in mM: 3 KCl, 26 NaHCO3, 1 NaH2PO4, 0.5 CaCl2), 3.5 MgSO4, 25 dextrose, 123 sucrose) for quick, less than 5 min, slicing on vibratome at a thickness of 450 μm. The sections then were placed into an oxygenated incubation ACSF solution (containing the following, in mM: 123 NaCl, 3 KCl, 26 NaHCO3, 1 NaH2PO4, 2 CaCl2), 6 MgSO4, 25 dextrose) for 40 min, maintained at 32-36° C. (Sadovsky et al., J Neurosci, 2013, 33:14048-676). Tissue was left to rest at room temperature for 30 min before hypoxic induction. Hypoxia was induced in brain slices (i.e., living acute brain sections) in an oxygen-deprived chamber for 5 min, while their opposite hemisphere counterparts were used as normally oxygenated controls.

In-Situ Gold Nanoparticles Biosynthesis

Three aliquots of aqueous $AuCl_3$ were added to oxygen-deprived and oxygenated (control) brain slices to reach 100 μM-10 mM final concentrations of the precursor, incubated for 5 min, thoroughly rinsed (to ensure removal of precursor excess), and fixed using 2% glutaraldehyde+2% paraformaldehyde in 0.1M phosphate buffer, pH 7.4, and then stored in the same fixing solution at +5° C. before imaging and analyses.

Au-based nanostructures are useful in biomedical applications owing to their high biocompatibility and in vivo stability. Moreover, the inherent antioxidant properties of Au NPs as various ROS scavengers add remarkable value to their tissue protection potential.

Synchrotron SAXS and WAXS Analyses

Before the beam experiment, brain slices were removed from the ACSF solution, and mounted by sealing them between two thin glass cover slides (Fisherfinest). In situ small-angle X-ray scattering (SAXS) and wide angle X-ray scattering (WAXS) (SAXS/WAXS) measurements were carried out at beamline 12-ID-B of the Advanced Photon Source (APS), Argonne National Laboratory. In situ SAXS data were analyzed by custom-built software that is run on Matlab after standard data correction including background correction.

TEM Imaging

To isolate Au NPs, fixed brain slices were freeze-dried and mechanically grinded down. Then the NPs were extracted by DI water followed by separation of the biological debris via centrifugation (2000 rpm for 10 min). The NPs-containing supernatant were dropped onto an Ultrathin Carbon Cu transmission electron microscopy (TEM) grid with the Formvar pre-removed in toluene. Samples were allowed to set for about 1 hour and then rinsed by DI water. TEM analysis of the NPs was performed with a JEM-2100F field emission electron microscope (JEOL LTD, Tokyo, Japan) operated at 200 kV.

Example 2

NADH Reduces Gold Precursors to Form Gold Nanoparticles

To determine if the strong electron donating ability of NADH cofactor (−320 mV/NHE) could drive biosynthesis of Au NPs from corresponding precursor in situ in the living brain experiments were conducted to test the reaction depicted in FIG. 1A in order to determine if an excess of reducing equivalents accumulated near a hypoxia site can be redirected to the metal ion reduction reaction, while the formed oxidized NAD+ became available to serve as a strong electron sink to restore the normal physiological NADH/NAD+ ratio and cellular respiration, and ultimately help protect the brain.

Ex situ experiments were conducted to prove that NADH can indeed reduce noble metal precursors, i.e., gold precursors, resulting in the formation of Au NPs and NAD. $AuCl_3$ was chosen as a precursor due to higher electron sinking capacity of Au (III) and higher stability as compared to Au(I) that can transform in vivo into Au(III) (Thakor et al., Nano Lett, 2011, 11: 4029-4036). Because NADH absorbs light at 340 nm, while its oxidized form does not (Rozhkova et al., J Biol Chem, 2002, 277: 16888-16894), and Au NPs exhibit plasmon resonance at 520 nm, the reaction was monitored spectroscopically by acquiring the UV-vis spectra.

Figure 1B:
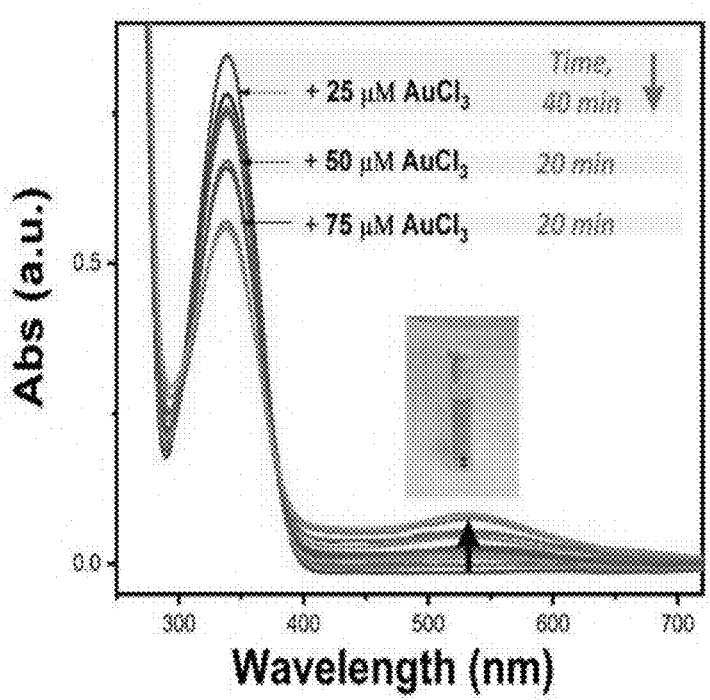

The introduction of $AuCl_3$ into a cuvette containing NADH aqueous solution ($AuCl_3$/NADH at a molar ratio of 1:4) resulted in the immediate drop of the intensity of peak at 340 nm, indicating the oxidation of NADH (FIG. 1b). However, a new peak at 520 nm, characteristic for Au NPs, appeared after ~7 min of the reaction, and continued to develop. Interestingly, the further increase of NPs was accompanied by a very minor oxidation of NADH, as evidenced by only a slight change in the peak intensity at 340 nm in the UV-vis spectra. After 20 min of the reaction, a pink color was detected by the naked eye (FIG. 1B, inset). Further additions of $AuCl_3$ to the reaction media were also accompanied by an immediate decrease of the absorbance at 340 nm followed by a slowdown of the NADH oxidation until reaching a plateau.

The oxidation of each NADH molecule results in the release of two electrons, whereas three electrons are required to reduce the $Au^{3+}$ ion to $Au^0$. Based on observations summarized in FIG. 1B, it can be concluded that the formation of the NP is influenced not only by the stoichiometry of the NADH and Au NPs precursor. In fact, formation of the Au NP appears to be a complex dynamic process where NADH provides the initial trigger for reduction of the metal ion and particle nucleation, and then, possibly, other simultaneous processes, e.g. metal-ligand complex formation, particle-precursor, particle-particle interactions, and/or particle-catalyzed NADH oxidation (Huang et al., Photoch Photobio B, 2005, 81:76-83) can take place.

Other types of gold precursors also were tested. While AuCl behaved similarly to $AuCl_3$, and was reduced by NADH to $Au^0$, biocompatible gold-thiolate complexes, such as auranofin, solganal and myochrysine, known for their use in chrysotherapy, being mixed with NADH yielded no Au NPs that can be attributed to high stability of the gold-thiolate bond under test conditions. However, the formation of Au NPs from gold-thiolate precursors cannot be ruled out in vivo, since a weak covalent gold-thiolate bond (dissociation energy 50 kJ/mol-100 kJ/mol) can be successfully reduced in the intracellular microenvironment, liberating gold ions (Xue et al., Nature Communications, 2014, 5).

Example 3

Experimental Hypoxia in Living Acute Brain Sections

Encouraged by the results of the ex situ experiments, an experimental animal living brain model was used in order to test the applicability of gold NP synthesis by NADH ex vivo. To determine if hypoxia could be prevented in the living brain, living acute brain sections were prepared from mice (C57BL/6J, male, 17 days old). All animal procedures and the brain slice preparation procedures were performed in accordance to the Institutional Animal Care and Use Committee at the University of Chicago.

Mice (n=2) were anesthetized by intraperitoneal injection of ketamine-xylazine, decapitated, and their brains were quickly removed. The brains were placed in ice-cold "cut" ACSF solution (containing the following, in mM: 3 KCl, 26 NaHCO3, 1 $NaH_2PO_4$, 0.5 $CaCl_2$), 3.5 $MgSO_4$ 25 dextrose, 123 sucrose) for quick, less than 5 min, slicing on vibratome at a thickness of 450 μm.

Coronal 450 μm thick sections of the mouse brain were isolated and prepared by a technique that allows maintaining the integrity of the isolated brain functions for sufficient experimental time-lapse, as depicted in FIGS. 4A-D. (See Sadovsky et al., J Neurosci, 2013, 33: 14048-U14676). The prepared living brain slices were incubated in a chamber with oxygenated ACSF solution (containing the following, in mM: 123 NaCl, 3 KCl, 26 NaHCO3, 1 NaH2PO4, 2 $CaCl_2$), 6 MgSO4, 25 dextrose) for 40 min, maintained at 32-36° C. (Sadovsky et al., J Neurosci, 2013, 33: 14048-14676). Tissue was left to rest at room temperature for 30 min before hypoxic induction. Hypoxia was induced in brain slices in an oxygen-deprived chamber for 5 min, while their opposite hemisphere counterparts were used as normally oxygenated controls. Hypoxia was induced by disabling the oxygen supply for 2 min, FIGS. 4A-D. Solution containing Au(III) precursor was applied to the right hemisphere of the brain section, while the left hemisphere was used as an untreated control. In addition, normally oxygenated brain sections were also exposed to the Au(III) precursor for comparison with hypoxic slices. After 5 min incubation with Au(III) precursor, the brain slices were thoroughly washed to ensure the removal of the excess of precursors, and then fixed with a mixture of 2% glutaraldehyde and paraformaldehyde. Only slices that underwent hypoxia and were treated with $AuCl_3$ revealed staining localized mainly in the outer regions of the brain section that is indicative of the presence of Au NPs.

In order to confirm the formation of Au NPs, simultaneous small and wide angle X-ray scattering (SAXS and WAXS, respectively) measurements were conducted. SAXS allows determining size, shape, size distribution and structural features of nanoscale inorganic (Li et al., Chem Rev, 2016, 116: 11128-11180; Kwon et al., Nat Mater, 2015, 14: 215-223) and biological species, including complex tissue, such as the brain (Yagi, J Phys Conf Ser, 2011: 272) while WAXS determines the crystalline structure of the inorganic particles.

Figure 2A:
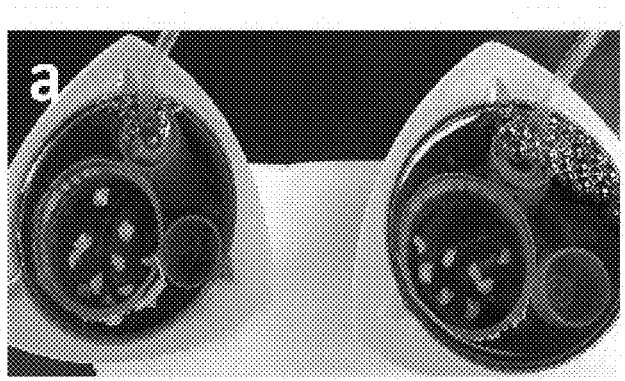
FIGS. 2A-G shows photographs and SAXS measurements of brain sections. Photographs of the 450 µm brain slices from two mice undergoing oxygenation prior to induction of hypoxia (FIG. 2A). The integrated SAXS intensities were obtained for the 4.5×4.5 mm area in the hypoxic brain section treated with Au (III) precursor (FIG. 2B) pinpointed as A, B, C and D within the 4.5×4.5 mm region (FIG. 2C). The plot shows SAXS curves at four representative positions (FIG. 2D).
Figure 2B:
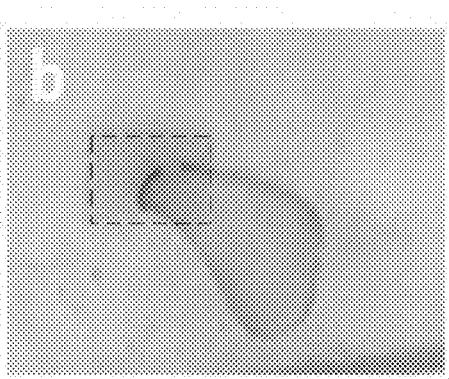
Figure 2C:
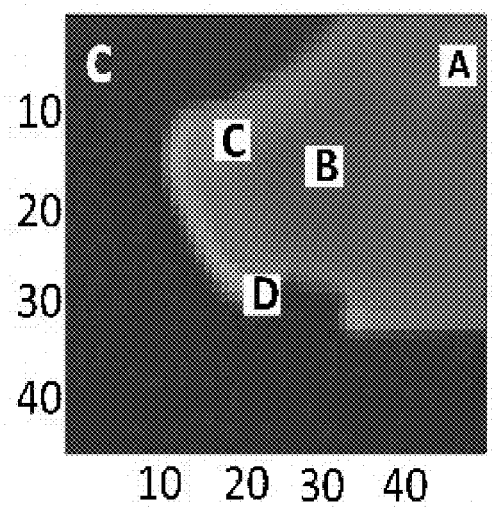
Figure 2D:
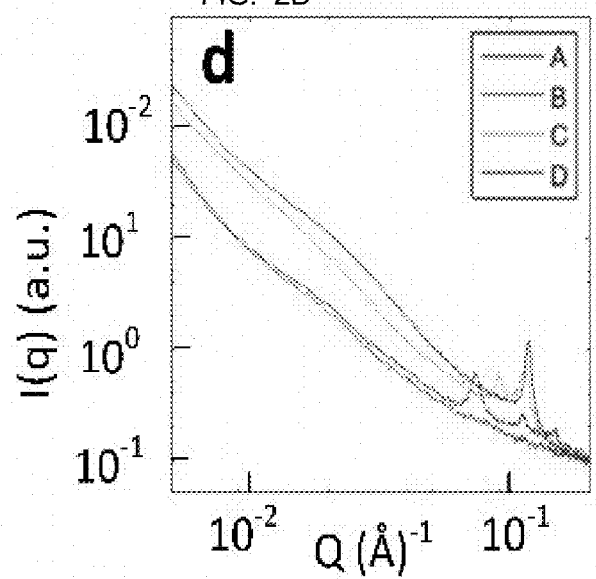
Figure 2E:
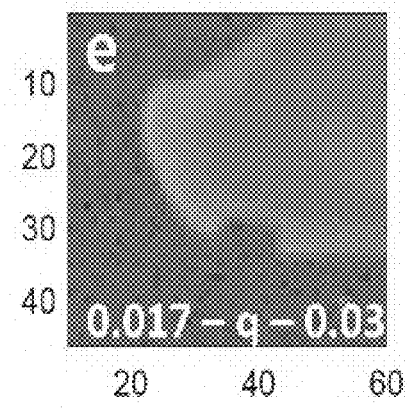
Figure 2F:
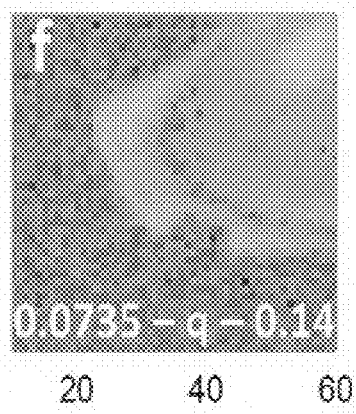
Figure 2G:
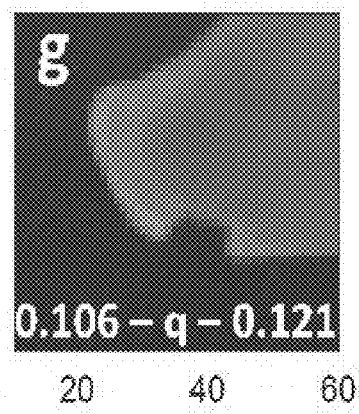

FIGS. 2A-D shows the integrated SAXS intensities in the broad q range and more narrow, feature-specific q regions. The SAXS patterns measured at positions A, C, and D shown in FIG. 2C demonstrate peaks at q~0.1 A-1, that can be characteristic for cell membranes (Yagi, (2011) supra) while no such peaks are detected at position B. The mapping result for this region is presented in FIG. 2F. Gold scattering is strong mostly at positions C and D that represent the outer areas of the brain that are stained by pink color. SAXS scattering peak indicating the presence of Au NPs at q~0.027 A-1 allows estimating the size of Au NPs as 23.31 nm (~2*pi/0.027). In contrast, the intensities of the WAXS signals were rather weak.

Figure 3A:
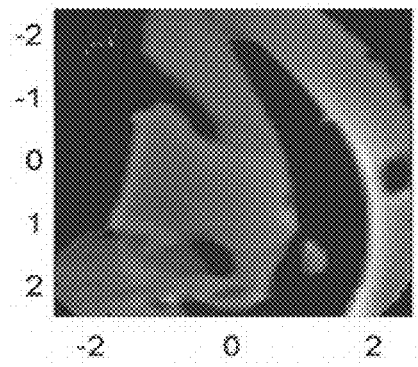
FIGS. 3A-I provide integrated SAXS intensities maps (FIG. 3A) obtained for hypoxic 450 µm-thick brain slice treated with 10 mM (×100 times higher concentration) of Au(III) precursor as compared to data shown in FIG. 2A-G. Plots of SAXS intensities in the selected (0.075-0.14) q range (3B) and WAXS integrated intensities of (111) reflection of Au (FIG. 3C). Optical image of the brain slice containing higher amount of the white matter (FIG. 3F) and corresponding integrated SAXS intensities maps (FIG. 3G, FIG. 3H) and WAXS integrated intensities (FIG. 3I) of (111) reflection of Au obtained for section of the brain shown in the white square in (FIG. 3F) demonstrating the representative TEM (FIG. 3D) and higher magnification TEM (FIG. 3E) images of the in-situ biosynthesized Au NPs. The inset in (FIG. 3D) shows the SAED pattern corresponding to the area shown in (FIG. 3F).
Figure 3B:
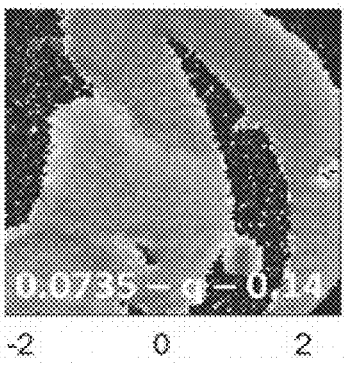
Figure 3C:
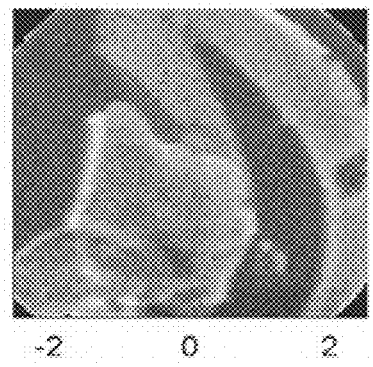
Figure 3D:
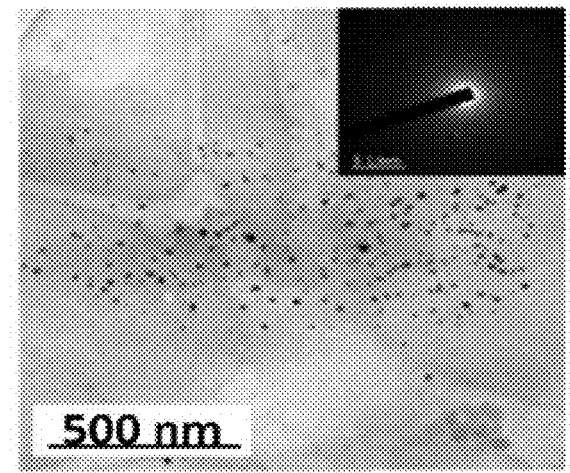
Figure 3E:
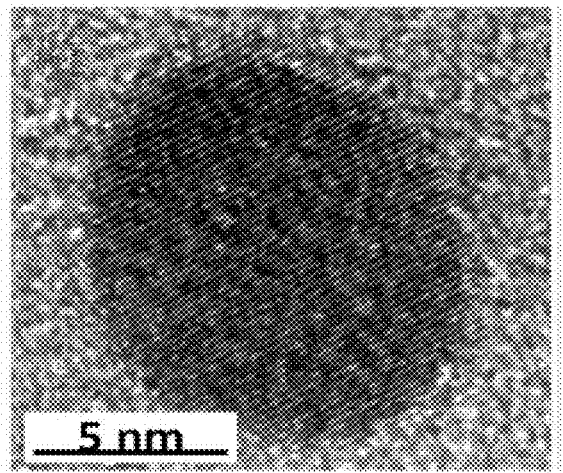
Figure 3F:
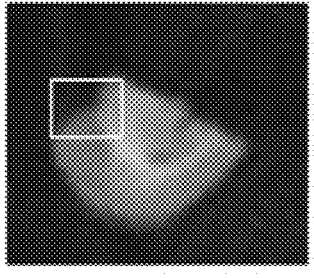
Figure 3G:
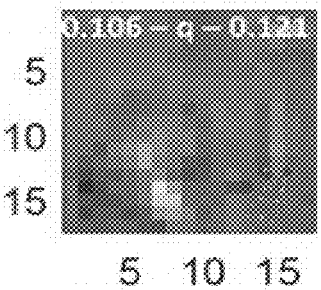
Figure 3H:
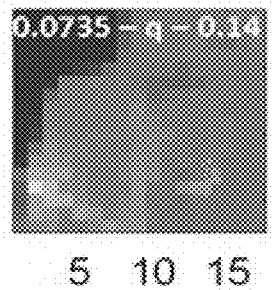
Figure 3I:
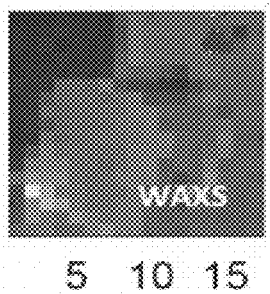
Figure 4B:
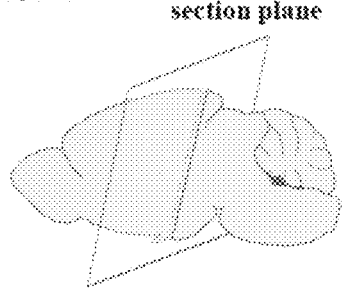
Figure 4B:
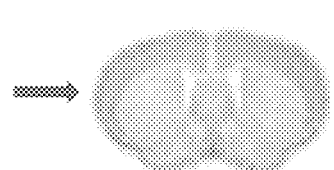
Figure 4C:
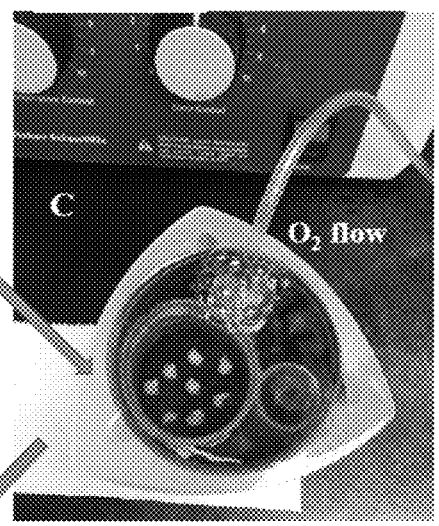
Figure 4D:
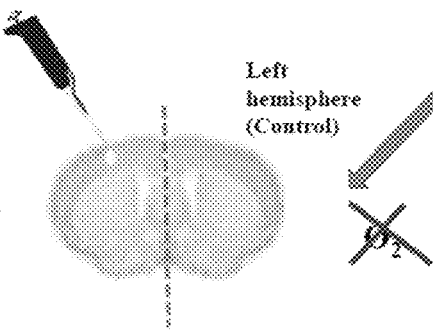

In order to enhance the intensities of the SAXS/WAXS signals, the concentration of Au(III) precursor was increased by 100 times (up to 10 mM). Again, the formation of Au NPs took place only in hypoxic brain slices (FIGS. 5A-B). The data obtained for hypoxic brain slices treated with higher Au(III) concentration are shown in FIG. 3A-I. The plots of SAXS intensities in the range corresponding to the formed NPs and WAXS integrated intensities of (111) reflection of Au shows a strong correlation (FIGS. 3B and 3C, respectively). The concentration of Au NPs is higher in the outer areas of the brain slice. The size of the Au NPs is estimated from the peak position of the SAXS spectrum as ~10 nm. Au NPs biosynthesized in situ in the hypoxic brain were isolated from the brain slices and visualized using the TEM. As demonstrated in FIGS. 3D-E, biosynthesized Au NPs are spherical and ~10 nm in diameter, which is consistent with the SAXS data.

Note, that in studies with lower and higher concentrations of the Au (III) precursor, the brains of different animals were used. Although the procedures for preparation and treatment of the brain for both animals were standard, and the difference in the size of biosynthesized Au nanoparticles can be explained by the difference in the initial concentration of Au (III) precursor, the influence of individual characteristics in biochemistry and anatomy of each animal cannot be excluded.

The Au NPs were formed only in the brain slices that underwent hypoxia. No Au NPs were detected in the presence of Au(III) precursor in the oxygenated brain slices. The SAXS/WAXS data on hypoxic brain treated with different Au(III) salt concentrations prove the formation of Au NPs. In both cases, the formation of Au NPs is localized closer to the surface of mouse brain while the sizes of particles at the surface and inner brain are the same. This observation indicates that all Au NPs nucleated and grew almost at the same time and this was mediated by the processes caused by hypoxia in the living brain.

The density of Au NPs was less pronounced within the white matter regions of the brain (FIG. 3F) where densely-packed lamellar structures material can be found (Yagi, J Phys Conf Ser, 2011, 272) as it is evidenced by SAXS/WAXS data (FIGS. 3F-3I). This result is expected since white matter contains myriads of axons, elongated neural cell "tails", which function as an electrical circuit connecting neurons, but are less involved in the NADH/NAD+ redox processes in the cell's body. Consequently, the probability of the formation of Au NPs in this tightly packed brain region is significantly lower due to lower permeability to the precursor on the one hand and less sensitivity to hypoxia on the other.

Biosynthesis of NPs is a striking phenomenon in nature. Inspiring examples include storage and transport of iron atoms in a non-toxic form of ferric oxyhydroxide cluster in the ferritin protein cage (Seckback, J Plant Nutr, 1982, 5:

369-394), using metal salts as terminal sinks in electron transfer pathways and formation of metal particles by bacteria (Caccavo et al., Appl Environ Microb, 1994, 60: 3752-9; Methe et al., Science, 2003, 302: 1967-9; Heidelberg et al., Nat Biotechnol, 2002, 20:1118-23), and biomineralization of magnetite nanocrystals in specific organelle magnetosome that enables coordinated movement of magnetotactic bacteria (Blakemore, Science, 1975, 190: 377-9). Under certain experimental conditions, metal complexes and nanoclusters can be obtained in mammalian cells or in a whole animal, mainly for use in imaging (Jin, et al., Colloids Surf B Biointerfaces, 2018, 163: 385-93; Ye et al., Biomater Sci-Uk, 2016, 4, 652-60; Wang et al., Sci Rep-Uk, 2013, 3; Pilapong et al., Mater Lett, 2015, 140:162-5; Gao et al., Sci Rep-Uk, 2014, 4; Chen et al., Acs Appl Mater Inter, 2015, 7: 18163-9; Fernandez et al., Biomaterials, 2015, 43:1-12). However, the mechanisms of these bio-synthesis are often spontaneous, poorly understood and, therefore, difficult to control. In the approach described herein, a pathological process initiates and controls biosynthesis of biocompatible Au nanoparticles from precursor salts in the immediate vicinity of the hypoxia site, thereby restoring the redox state of the brain.

These experiments demonstrated a proof of a concept, i.e., the redirection of the pathological biochemical process of accumulation of reduced pyridine nucleotides under deleterious hypoxic conditions in the brain toward the reduction of the precursor salt and biosynthesis of biologically compatible, antioxidant Au0 NPs and the simultaneous restoring of the tissue redox status. The proposed concept of biosynthesis of Au NPs triggered by a misbalance of the cellular pathological process (e.g., here by hypoxia), can complement the more classical use of pre-synthetized Au NPs, which are among the most popular diagnostic imaging and therapeutic NP agents (Thakor et al., Nano Lett, 2011, 11: 4029-36; Dreaden et al., Chemical Society Reviews, 2012, 41: 2740-79).

Such approach is applicable in other highly metabolic tissues and organs that are particularly vulnerable to oxygen deficiencies, including the heart, kidney, and liver. Besides, combined with innovative technologies for preserving and restoring the functions of isolated tissue at ambient conditions, for example BEx technology (Vrselja et al., Nature, 2019, 568: 336), the products and methods as described herein can be utilized in organ transplantation and recovery and in combinatorial screening of anti-hypoxia therapeutics on isolated sections of the living brain, as well as for detection of abnormally elevated levels of the reducing equivalents, e.g., NAD(P)H, GSH, and $TrxSH_2$, in cells, tissues, and/or organs. In various aspects, cells, tissues, and/or organs includes biopsied material and/or isolated cell, tissues, and/or organs.

While the present disclosure has been described in terms of specific embodiments, it is understood that variations and modifications will occur to those skilled in the art. Accordingly, only such limitations as appear in the claims should be placed on the disclosure.

All documents referred to in this application are hereby incorporated by reference in their entirety.

We claim:

1. A method of preserving an isolated cell, tissue, or organ ex vivo for transplantation, the method comprising:
   administering ex vivo to the isolated cell, tissue, or organ an effective amount of a noble metal precursor to form a noble metal nanoparticle in situ and increase the ratio of oxidized to reduced forms of nicotinamide adenine dinucleotide (NAD+/NADH), nicotinamide adenine dinucleotide phosphate (NADP+/NADPH), glutathione (GSSG/GSH), or thioredoxin (TrxSS/$TrxSH_2$) in the isolated cell, tissue, or organ;
   wherein the noble metal precursor is selected from the group consisting of a noble metal halide, a noble metal hydroxide, a noble metal chloride, a complex of any one of the foregoing with one or more organic ligands, and combinations thereof; and
   wherein the noble metal of the precursor is selected from the group consisting of gold (Au), silver (Ag), platinum (Pt), palladium (Pd), ruthenium (Ru), rhodium (Rh), osmium (Os), and iridium (Ir).

2. The method of claim 1, wherein increasing the ratio of NAD+/NADH, NADP+/NADPH, GSSG/GSH, or TrxSS/$TrxSH_2$ reduces production of reactive oxygen species, reduces reactive nitrogen species, and/or reduces apoptosis.

3. The method of claim 1, wherein the noble metal nanoparticle reduces the accumulation of reduced pyridine nucleotides in the cell, tissue, or organ.

4. The method of claim 1, wherein the cell, tissue, or organ is suffering from or is at risk of suffering from a deficiency of oxidized forms of nicotinamide adenine dinucleotide (NAD+), nicotinamide adenine dinucleotide phosphate (NADP+), glutathione (GSSG), or thioredoxin (TrxSS).

5. The method of claim 1, wherein the noble metal precursor is a gold chloride.

6. The method of claim 5, wherein the gold chloride is gold monochloride (AuCl), gold dichloride ($AuCl_2$), gold trichloride ($AuCl_3$), tetragold octachloride ($Au_4Cl_8$), or chloroauric acid ($HAuCl_4$).

7. The method of claim 1, wherein the cell is a brain cell, a cardiac cell, a kidney cell, a lung cell, a liver cell, a stomach cell, an intestinal cell, a pancreatic cell, a blood cell, a retinal cell, a skin cell, or other cell of the eye.

8. The method of claim 1, wherein the cell is a non-cancerous tumor cell.

9. The method of claim 1, wherein the tissue is isolated from the brain, the heart, the kidney, the lung, the liver, the stomach, the intestine, the pancreas, the blood, the retina, or the skin.

10. The method of claim 1, wherein the organ is the heart, the kidney, the lung, the liver, the stomach, the intestine, the pancreas, the blood, the retina, or the skin.

11. The method of claim 1, wherein the effective amount is from about 0.1 pmol/g to about 1 mol/g.

12. The method of claim 1, wherein the effective amount is administered at a concentration from about 1 nM to about 1 M.

* * * * *